United States Patent [19]
Siczek et al.

[11] Patent Number: 5,803,912
[45] Date of Patent: Sep. 8, 1998

[54] POSITIONING FUNCTION MAMMOGRAPHIC BIOPSY FUNCTION SYSTEM WITH OFFSET

[75] Inventors: Bernard Siczek, Boulder; Menachem Assa, Englewood; Michael A. DePourbaix, Arvada, all of Colo.

[73] Assignee: Fischer Imaging Corporation, Denver, Colo.

[21] Appl. No.: 428,563

[22] Filed: Apr. 25, 1995

Related U.S. Application Data

[63] Continuation of Ser. No. 18,805, Feb. 17, 1993, Pat. No. 5,415,169, which is a continuation-in-part of Ser. No. 817,722, Jan. 7, 1992, abandoned, which is a continuation of Ser. No. 440,775, Nov. 21, 1989, Pat. No. 5,078,142, and Ser. No. 799,418, Nov. 27, 1991, Pat. No. 5,240,011.

[51] Int. Cl.$^6$ ...................................................... A61B 5/00
[52] U.S. Cl. .............................. 600/407; 378/37; 378/205
[58] Field of Search ................................ 128/653.1, 630; 606/130; 378/37, 205, 163; 600/300, 407, 437, 440, 473; 601/4, 2

[56] References Cited

U.S. PATENT DOCUMENTS

| | | | |
|---|---|---|---|
| 2,707,662 | 5/1955 | Goldfield et al. | 311/6 |
| 3,165,630 | 1/1965 | Bielat et al. | 250/58 |
| 3,609,355 | 9/1971 | Schwarzer | 250/50 |
| 3,963,933 | 6/1976 | Henkes, Jr. | 250/456 |
| 3,973,126 | 8/1976 | Redington et al. | 250/444 |
| 4,051,380 | 9/1977 | Lasky | 250/451 |
| 4,099,880 | 7/1978 | Kano | 356/164 |
| 4,485,819 | 12/1984 | Igl | 128/660 |
| 4,545,385 | 10/1985 | Pirschel | 128/660 |
| 4,605,011 | 8/1986 | Naslund | 128/752 |
| 4,613,122 | 9/1986 | Mannabe | 269/322 |
| 4,618,973 | 10/1986 | Lasky | 378/37 |
| 4,727,565 | 2/1988 | Ericson | 378/205 |
| 4,750,487 | 6/1988 | Zanetti | 128/303 |
| 4,791,934 | 12/1988 | Brunnett | 128/653 |
| 4,869,247 | 9/1989 | Howard, III et al. | 128/303.1 |
| 4,875,478 | 10/1989 | Chen | 128/303 |
| 4,890,311 | 12/1989 | Saffer | 378/99 |
| 4,930,143 | 5/1990 | Lundgren et al. | 378/37 |

(List continued on next page.)

FOREIGN PATENT DOCUMENTS

| | | |
|---|---|---|
| 2640248 | 3/1978 | Germany . |
| 7805393 | 6/1980 | Sweden . |

OTHER PUBLICATIONS

"Stereotaxic Instrument for Needle Biopsy of the Mamma", Bolmgren et al., *Am. J. Roentgenol*, 129, pp. 121–125 (Jul., 1977).

"The Needle Replaces the Knife –Exploring Stereotactic Guided Needle Biopsy", Dowlatshahi, *Administrative Radiology*, Jun., 1989, pp. 28–31.

"Radiologists Spread Their Wings: A Look at the Possibilities in Stereotactic Breast Biopsy", Haight et al., *Administrative Radiology*, Nov., 1987, pp. 87–89.

(List continued on next page.)

*Primary Examiner*—Marvin M. Lateef
*Assistant Examiner*—Shawna J. Shaw
*Attorney, Agent, or Firm*—Holme Roberts & Owen LLP

[57] ABSTRACT

A motorized biopsy needle positioner employed in a mammographic needle biopsy system receives coordinate information representative of an identified point of interest within a patient's captive breast under examination and automatically positions a biopsy needle in accordance with that coordinate information to permit insertion of the biopsy needle to the identified point of interest. An offset mode of operation of the motorized biopsy needle positioner automatically positions the biopsy needle in accordance with coordinate information representative of an offset point within the patient's breast that is offset from the previously identified point of interest to permit insertion of the biopsy needle to that offset point. A manual mode of operation of the motorized biopsy needle positioner permits the user to actuate directional keys of a user control unit to position the biopsy needle in one or more directions, as specified by the actuated directional keys.

7 Claims, 15 Drawing Sheets

U.S. PATENT DOCUMENTS

| | | | |
|---|---|---|---|
| 4,958,625 | 9/1990 | Bates et al. | 128/754 |
| 4,967,762 | 11/1990 | Devries | 128/753 |
| 4,989,614 | 2/1991 | Dejter, Jr. et al. | 128/752 |
| 5,027,827 | 7/1991 | Cody et al. | 128/753 |
| 5,036,860 | 8/1991 | Leigh et al. | 128/754 |
| 5,048,538 | 9/1991 | Terwilliger et al. | 128/754 |
| 5,078,142 | 1/1992 | Siczek et al. | 128/653 |
| 5,081,984 | 1/1992 | Wess et al. | |
| 5,125,413 | 6/1992 | Baran | 128/754 |
| 5,146,921 | 9/1992 | Terwilliger et al. | 128/754 |
| 5,249,581 | 10/1993 | Horbal et al. | |
| 5,285,772 | 2/1994 | Rattner | |
| 5,295,483 | 3/1994 | Nowacki et al. | |
| 5,350,351 | 9/1994 | Saffer | |
| 5,409,001 | 4/1995 | Seyler et al. | |

OTHER PUBLICATIONS

"Stereotactic Needle Biopsy", Svane, *Administrative RAdiology*, Nov., 1987, pp. 90–92.

"Stereotactic Fine–Needle Biopsy in 2594 Mammographically Detected Non–Palpable Lesions", Azavedo et al., reprinted from *The Lancet*, May 13, 1989, pp. 1033–1036.

"Needle Localization and Fine–Needle Aspiration Biopsy of NonPalpable Breast Lesions with Use of Standard and Stereotactic Equipment", Evans et al., *Radiology*, vol. 173, No. 1, Oct. 1989, pp. 53–56.

"Nonpalpable Breast Tumors: Diagnosis with Stereotaxic Localization and Fine–Needle Aspiration", Dowlatshahi et al., *Radiology*, vol. 179, No. 2, Feb., 1989, pp. 427–433.

TRC Mammotest Diagnostic System for Breast Cancer, not dated (6 pages).

TRC Mammotest System manufacturing drawings, not dated (11 sheets).

TRC Mammotest Manual, not dated (17 pages).

Phillips Medical Systems "Operator's Manual –Cytoguide Stereotactic Biopsy System".

5,803,912

POSITIONING FUNCTION MAMMOGRAPHIC BIOPSY FUNCTION SYSTEM WITH OFFSET

REFERENCE TO RELATED PATENT APPLICATIONS

This application is a continuation of U.S. patent application Ser. No. 08/018,805 filed Feb. 17, 1993, now U.S. Pat. No. 5,415,169 entitled "Motorized Mammographic biopsy Apparatus" which is a continuation-in-part of U.S. patent application Ser. No. 07/817,722 filed Jan. 7, 1992, now abandoned, entitled "Precision Mammographic Needle Biopsy System", which in turn, is a continuation of U.S. patent application Ser. No. 07/440,775 entitled "Precision Mammographic Needle Biopsy Systems", now U.S. Pat. No. 5,078,142, and U.S. Patent application Ser. No. 07/799,418 filed Nov. 27, 1991 entitled "Motorized Biopsy Needle Positioner", now U.S. Pat. No. 5,240,011.

BACKGROUND OF THE INVENTION

This invention relates generally to mammography biopsy systems that are designed to detect and obtain cell or tissue samples from non-palpable lesions of the female breast. More particularly, this invention is directed to an advanced mammographic needle biopsy system incorporating a motorized biopsy needle positioner that automatically positions a biopsy needle to allow insertion to an identified point of interest in a patient's breast that is under examination.

Mammographic needle biopsy systems, such as a Mammotest system manufactured and marketed by Fischer Imaging Corporation, Denver, Colo., employ a computer-digitizer system to digitize the location of a point of interest within the patient's breast as that point of interest appears on a pair of stereo x-rays of the breast and to thereafter compute the three-dimensional or spatial coordinates of that point of interest and display them to the user. The user then manually sets these three-dimensional coordinates into respective position controls for a puncture instrument assembly and inserts a biopsy or other needle to the identified point of interest. These manual systems are susceptible to human error in setting the computed coordinates of the point of interest into the puncture instrument. In addition, manual setting of the coordinates of the point of interest is a time consuming operation that is frustrating to the patient, who is required to continue holding a position in which one of her breasts is under compression. Also, the clinician user is not permitted the flexibility of inserting the biopsy needle to a point within the patient's breast that is slightly offset from the previously identified point of interest because the coordinates provided by the computer-digitizer correspond only to the identified point of interest. It will be appreciated that such offset insertion in the present invention facilitates multiple pass sampling of a breast lesion using a driven biopsy instrument or other biopsy instrument as may be desired.

SUMMARY OF THE INVENTION

It is therefore a principal object of the present invention to provide a motorized biopsy needle positioner for mammographic needle biopsy systems that automatically positions a biopsy needle to permit insertion of the needle to an identified point of interest within a patient's breast, and preferably to points offset therefrom for multiple pass sampling.

It is a further object of the present inventions to provide a motorized biopsy needle positioner for mammographic needle biopsy systems that includes a control unit for enabling the user to manually position a biopsy needle to allow insertion of the needle to a point within a patient's breast that is spatially offset from an identified point of interest.

It is an additional object of the present invention to provide an improved mammographic needle biopsy system in which a digitizer is employed to digitize the location of a point of interest within the patient's breast that appears on a pair of stereo X-rays that do not have coordinate scales depicted thereon and in which the vertical angle, horizontal angle, and insertion depth parameters defining that point of interest are automatically calculated and can be utilized by a motorized biopsy needle positioner to automatically position a biopsy needle with respect to at least some of these parameters.

It is another object of the present invention to provide an improved mammographic needle biopsy system in which a motorized biopsy needle positioner is used in conjunction with an examination table having an opening through which the patient's breast is permitted to pendulantly protrude so as to achieve highly accurate biopsy needle positioning.

It is a further object of the present invention to provide an improved mammographic needle biopsy system combinatively employing automatic positioning and offset features with a driven biopsy needle assembly which may comprise a spring loaded biopsy gun for rapid biopsy needle insertion into a patient's breast to obtain a tissue sample.

It is yet another object of the present invention to provide an improved mammographic needle biopsy system for combinatively immobilizing and imaging a pendulant breast disposed in a predetermined relationship to a predetermined frame of reference, automating the identification and spatial coordinate computation of a point of interest within the pendulant breast relative to the predetermined frame of reference, supportably disposing a driven biopsy needle assembly, or puncture instrument, in predetermined relation to the predetermined frame of reference, and automating the positioning of the driven biopsy needle assembly to permit insertion of a biopsy needle within the breast to the point of interest.

According to one embodiment of the present invention, an apparatus is provided for use in inserting a biopsy needle to a point of interest within a patient's captive breast. The apparatus comprises: a biopsy needle positioner for controllably retaining a biopsy needle for movement within a spatial coordinate system that encompasses the patient's captive breast, the biopsy needle positioner being motorized for positioning a biopsy needle in accordance with specified coordinates of a spatial coordinate system; a controller, coupled to the biopsy needle positioner, for receiving coordinate information that specifies the coordinates of a point of interest within the patient's captive breast; a user control mechanism, coupled to the biopsy needle positioner, for enabling a user to initiate automatic movement of a biopsy needle in accordance with coordinate information received by the controller; and, preferably, an offset control mechanism for controlling the biopsy needle positioner to move a biopsy needle in accordance with offset coordinate information pertaining to an offset point that is spatially offset from the point of interest so as to permit insertion of a biopsy needle to the offset point. The apparatus can further include a second user control mechanism for enabling the user to initiate manual movement of the biopsy needle and a mechanism for designating movement of the biopsy needle in one or more selected directions. Moreover, the apparatus can include a safety interlock, actuable by the user, for preventing inadvertent movement of the biopsy needle.

In accordance with another embodiment of the present invention, an apparatus for performing medical procedures on a pendulant breast of a patient in a prone position comprises: a table for supporting a patient in a prone position, the table having a breast apperture therein through which one of the patient's breasts is permitted to pendulantly protrude in a position within a predetermined frame of reference; a mechanism for compressing the pendulant breast of the prone patient into a mammographic position relative to the predetermined frame of reference; a transmitter and receiver, positionable relative to the predetermined frame of reference, for imaging the pendulant breast; an identifier for identifying a location of interest within the pendulant breast so as to permit determination of three dimensional coordinates of the identified location of interest; and a motorized mechanism for positioning a medical instrument, e.g. biopsy needle, relative to the predetermined frame of reference so as to permit the instrument to be inserted within the pendulant breast to the location of interest.

In accordance with a still further embodiment of the present invention, an apparatus for use in performing medical procedures on a patient's breast comprises: a mechanism for immobilizing a patient's breast in a mammographic position relative to a predetermined frame of reference; a transmitter and receiver, located in predetermined relation to and positionable relative to the predetermined frame of reference, for imaging the patient's breast; an identifier for identifying a location of interest within the patient's breast so as to permit determination of three dimensional coordinates of the identified location of interest; a driven retainer for retaining and driving a hollow tip biopsy needle within the patient's breast to obtain a tissue sample from the location of interest; and a motorized positioner for positioning the driven retainer relative to the predetermined frame of reference, wherein upon activating the driven retainer, the hollow tip biopsy needle is positionable within the patient's breast at the location of interest to obtain a tissue sample.

The present invention can advantageously be utilized to obtain a tissue sample suitable for histological diagnosis from a breast lesion. As is well known, such tissue samples yield a far greater degree of diagnostic information than can be obtained from cell samples asperated according to conventional techniques. The combination of features employed in the present invention provides increased accuracy and reliability to faciliate this contemplated histological purpose.

DETAILED DESCRIPTION OF THE INVENTION

The present invention is directed to mammographic systems which incorporate motorized positioners for positioning a medical instrument at a point of interest within a patient's breast. It will be appreciated that such a motorized positioner can be incorporated into a variety of mammographic systems. Such a motorized positioner is described below in connection with FIGS. 1–6. Thereafter, a particular embodiment of a mammographic system incorporating a motorized positioner is described in connection with FIGS. 7–15.

Figure 1:
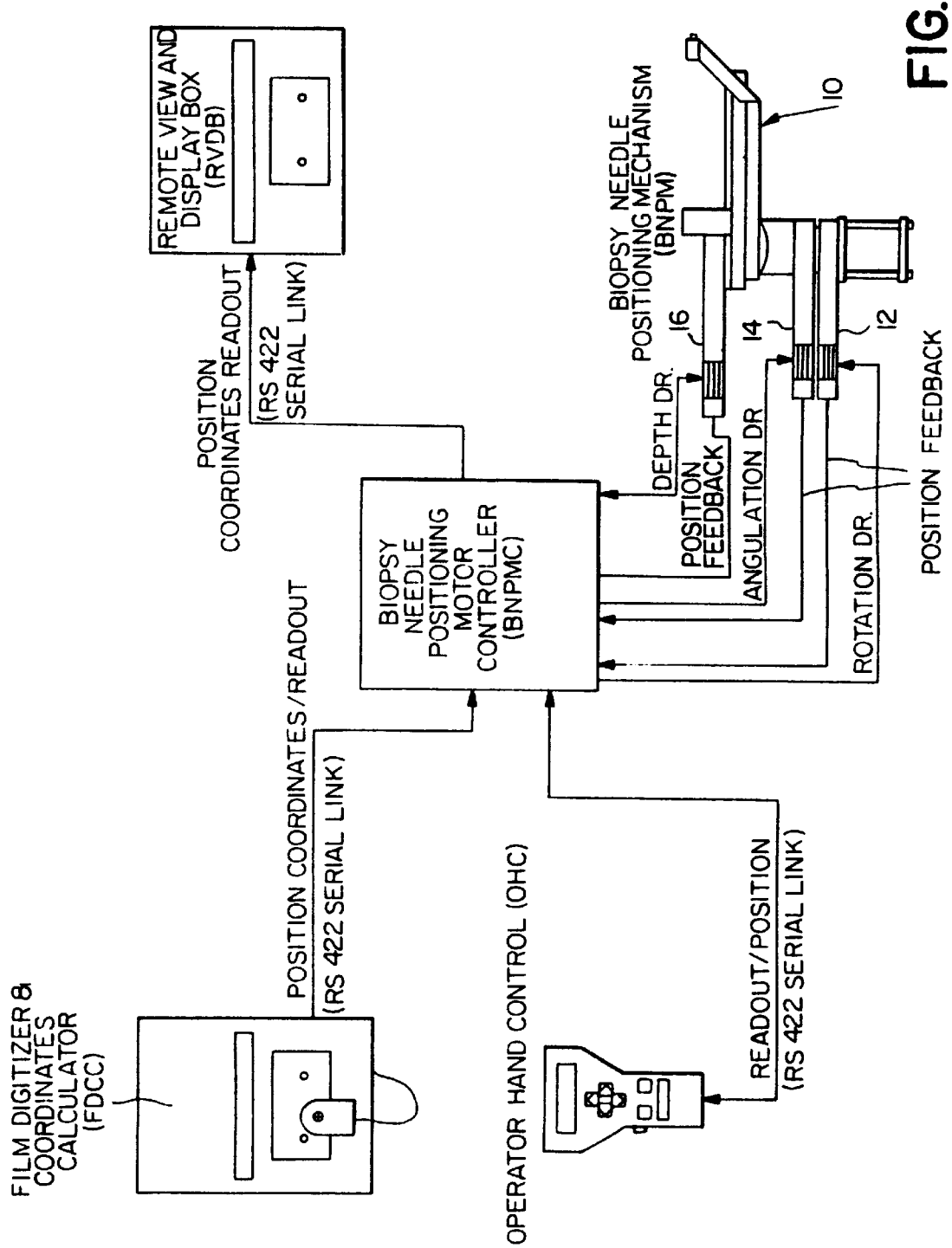
FIG. 1 is an overall block diagram of the motorized biopsy needle positioner of the present invention.
Figure 2:
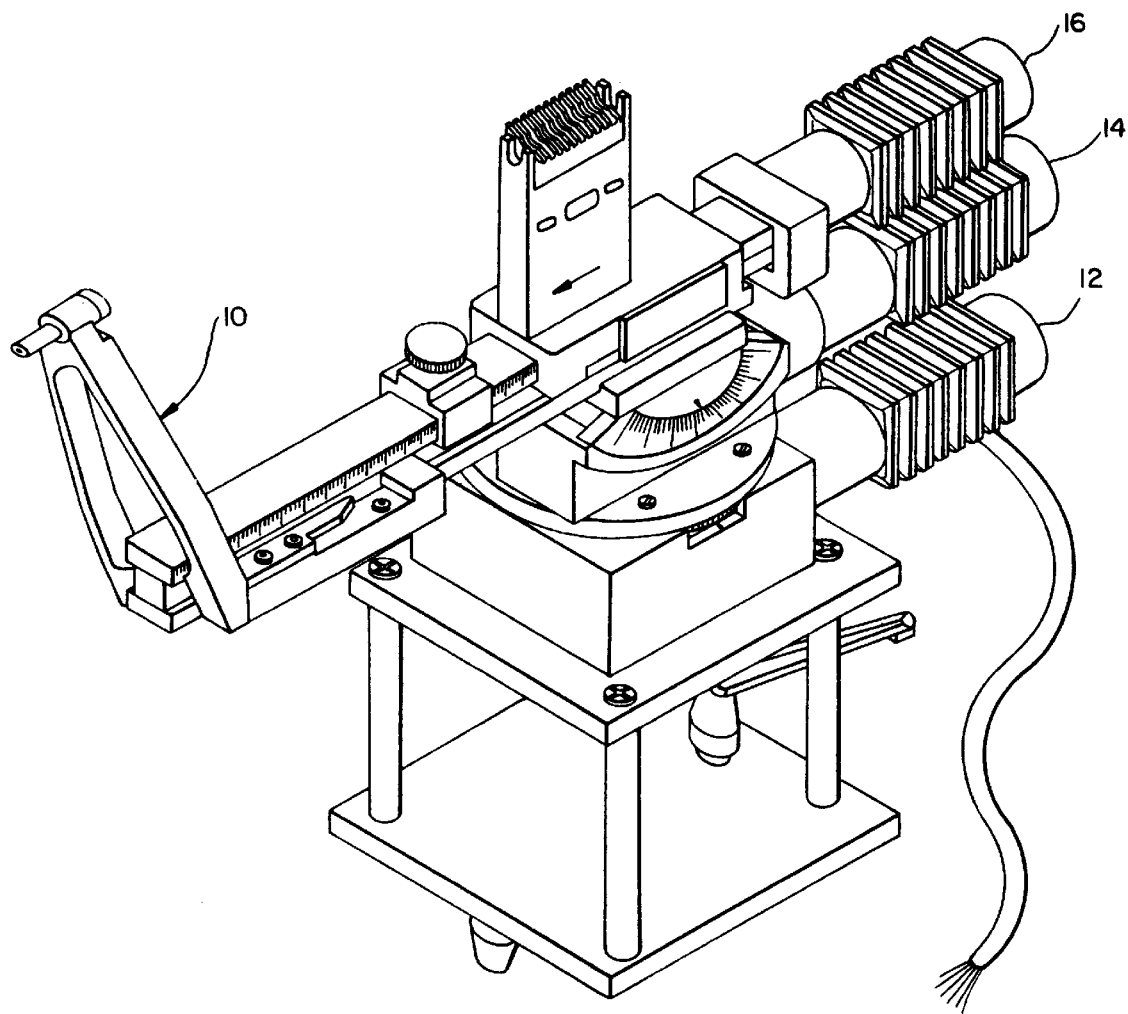
FIG. 2 is a pictorial diagram illustrating the biopsy needle positioning mechanism employed in the motorized biopsy needle positioner of FIG. 1.

Referring now to the block diagram of FIG. 1, there is shown a motorized biopsy needle positioner that includes a film digitizer and coordinates calculator FDCC, a biopsy needle positioning motor controller BNPMC, a biopsy needle positioning mechanism BNPM, an operator hand controller OHC, and a remote view and display box RVDB. The film digitizer and coordinates calculator, an embodiment of which is described in more detail below in connection with FIGS. 7–15, operates to digitize a point of interest in a patient's breast under examination and to thereafter compute and display the three-dimensional or spatial coordinates of the digitized point of interest. Although the invention will be described with respect to a polar coordinate system, the three-dimensional or spatial coordinates of the point of interest can be expressed in polar coordinates, an X, Y, and Z rectangular coordinate system or other spatial coordinate system.

The biopsy needle positioning motor controller receives the computed spatial coordinates of an identified point of interest from the film digitizer and coordinates calculator and drives three conventional DC motors that serve to control a puncture instrument in its rotation (horizontal) and angulation (vertical) axes, and to set a stop position along its depth axis to position a biopsy needle or other device retained by the puncture instrument for insertion to the identified point of interest within the patient's breast. It will be appreciated that particular positional adjustments, e.g., the setting of the stop position along the depth axis, can be performed manually in accordance with the present invention The biopsy needle positioning mechanism, illustrated in the detailed diagram of FIG. 2, and typically employed as a component of an overall mammographic needle biopsy system, comprises a conventional puncture instrument 10 for retaining a biopsy needle or other biopsy or therapeutic delivery device (not illustrated). Three conventional DC motors 12, 14, and 16 are provided for moving the biopsy needle retained by the puncture instrument 10 in the rotation and angulation axes and for setting a stop position along the depth axis, respectively. Positional feedback is provided to the biopsy needle positioning motor controller by the three DC motors 12, 14, and 16.

The operator hand controller allows the clinician user to control the motorized biopsy needle positioning system. Controls are provided to permit the user to initiate movement of the biopsy needle into a position for insertion to the identified point of interest within the patient's breast, in accordance with the computed spatial coordinates of that point of interest. The position of the biopsy needle may be monitored by the user with reference to a 32-character display on the operator hand controller. An enable switch is provided to prevent inadvertent motion of the biopsy needle.

The remote view and display box receives the spatial coordinates of rotation, angulation, and depth from the biopsy needle positioning ,motor controller and displays them for the benefit of the clinician user or others on a 40-character alphanumeric display. The remote view and display box may be conveniently mounted on a table that includes means for mounting and lighting x-ray reference films to be viewed during a breast biopsy procedure.

Figure 3:
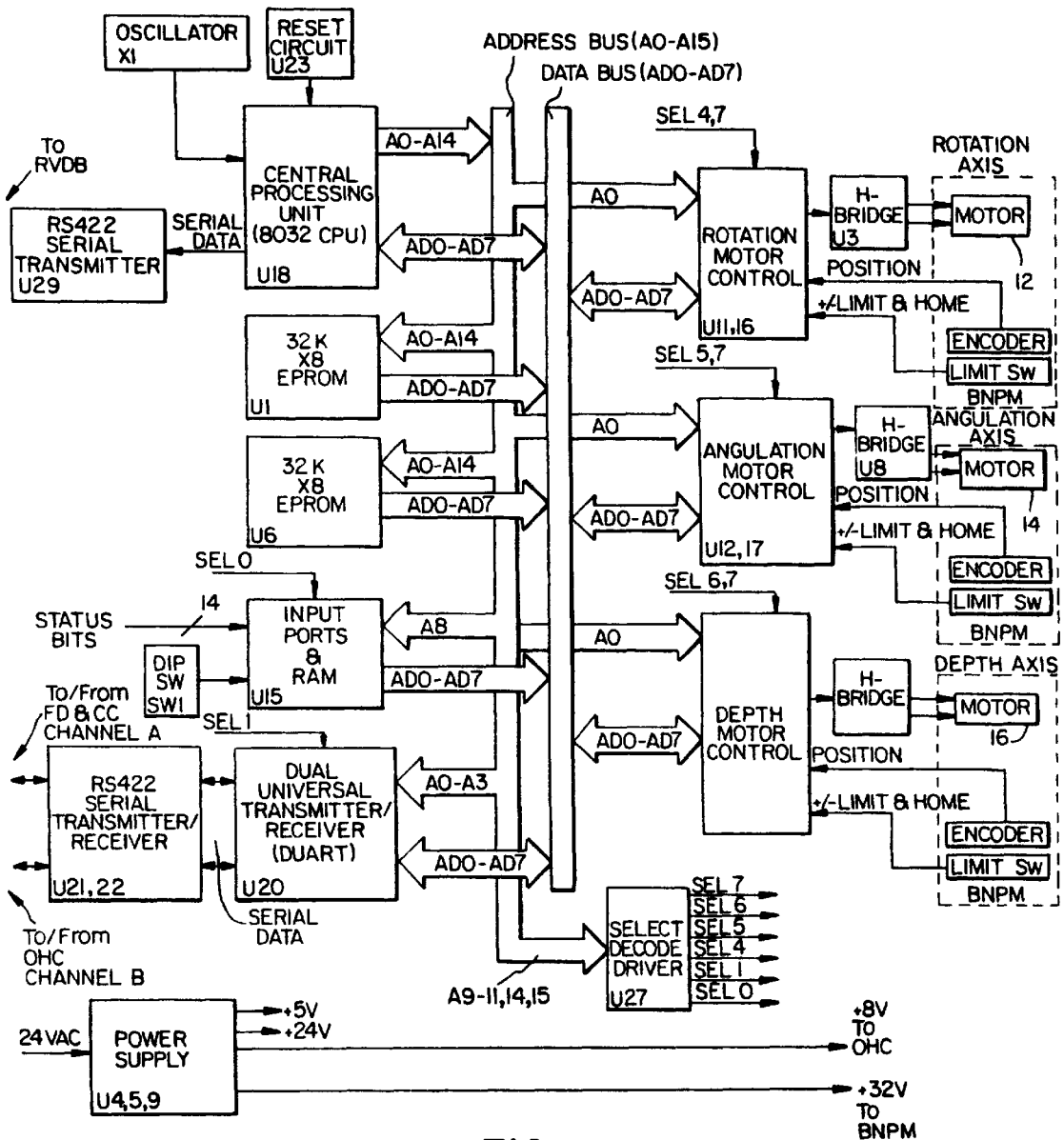
FIG. 3 is a detailed block diagram of the biopsy needle positioning motor controller of FIG. 1.

Operation of the biopsy needle positioning motor controller may be understood with reference to the detailed block diagram of FIG. 3. The biopsy needle positioning motor controller receives the spatial coordinates of the identified point of interest/within the patient's breast from the film digitizer and coordinates calculator and computes the variables required to drive the three DC motors 12, 14, and 16 that form part of the biopsy needle positioning mechanism. Information regarding the position of the biopsy needle is continuously provided by the biopsy needle positioning motor controller to the LED displays in the operator hand controller. During manual operation, the biopsy needle positioning motor controller receives commands from the operator hand controller and drives the biopsy needle positioning mechanism in the direction specified for as long as the user simultaneously depresses one of the direction arrow keys and the enable switch located on the operator hand controller illustrated in FIG. 4.

A central processing unit (8032 CPU) within the biopsy needle positioning motor controller has a direct serial communications link with the remote view and display box through an RS422 serial transmitter U29. The 8032 CPU also has two bi-directional communications links through a dual synchronous universal transmitter/receiver DUART, which provides serial communications between the biopsy needle positioning motor controller and both the film digitizer and coordinates calculator (serial channel B) and the operator hand controller (serial channel A).

Under normal operating conditions, the 8032 CPU loads the three DC motor controller sections (rotation, angulation, and depth) with high level initial conditions data. This initial conditions data includes velocity constants, acceleration constants, PID filter information, and sample period. When the spatial coordinates of the identified point of interest within the patient's breast, as computed by the film digitizer and coordinates calculator, are placed on the data bus AD0–AD7 by DUART U11, the 8032 CPU reads these spatial coordinates and calculates the corresponding motor control values. The 8032 CPU then sends this data to the three motor control sections. The motor control sections calculate the actual motor drive voltages and provide the drive voltages; to motors 12, 14, and 16 through separate H-bridge circuits. The motor control sections monitor the encoder feedback from the biopsy needle positioning mechanism to determine the position of the biopsy needle and to adjust the motor drive voltages as the biopsy needle reaches the identified point of interest. A typical motor voltage and velocity profile is trapezoidal in nature, ramping up to a start voltage, then holding constant, and finally ramping down to a stop voltage when the biopsy needle has reached the position required for insertion to the identified point of interest.

The 8032 CPU support circuits include operating and debug program data in erasable programmable read-only memories EPROMs U1 and U6. Fourteen status bits plus a six-bit DIP switch are monitored through an input port and a random access memory RAM U15. The status bits include +/− limit switches and a home switch associated with each coordinate axis. Two additional status bits serve to monitor the +5-volt (+5ENC) and +24-volt (+24VOK) power supplies. A reset circuit U23 provides a reset signal to reset the 8032 CPU when power is initially applied. The reset circuit also monitors program execution by counting a pulse associated with each cycle of the program and by executing a CPU reset command if the pulses stop, as may occur during a software lockup.

Figure 4:
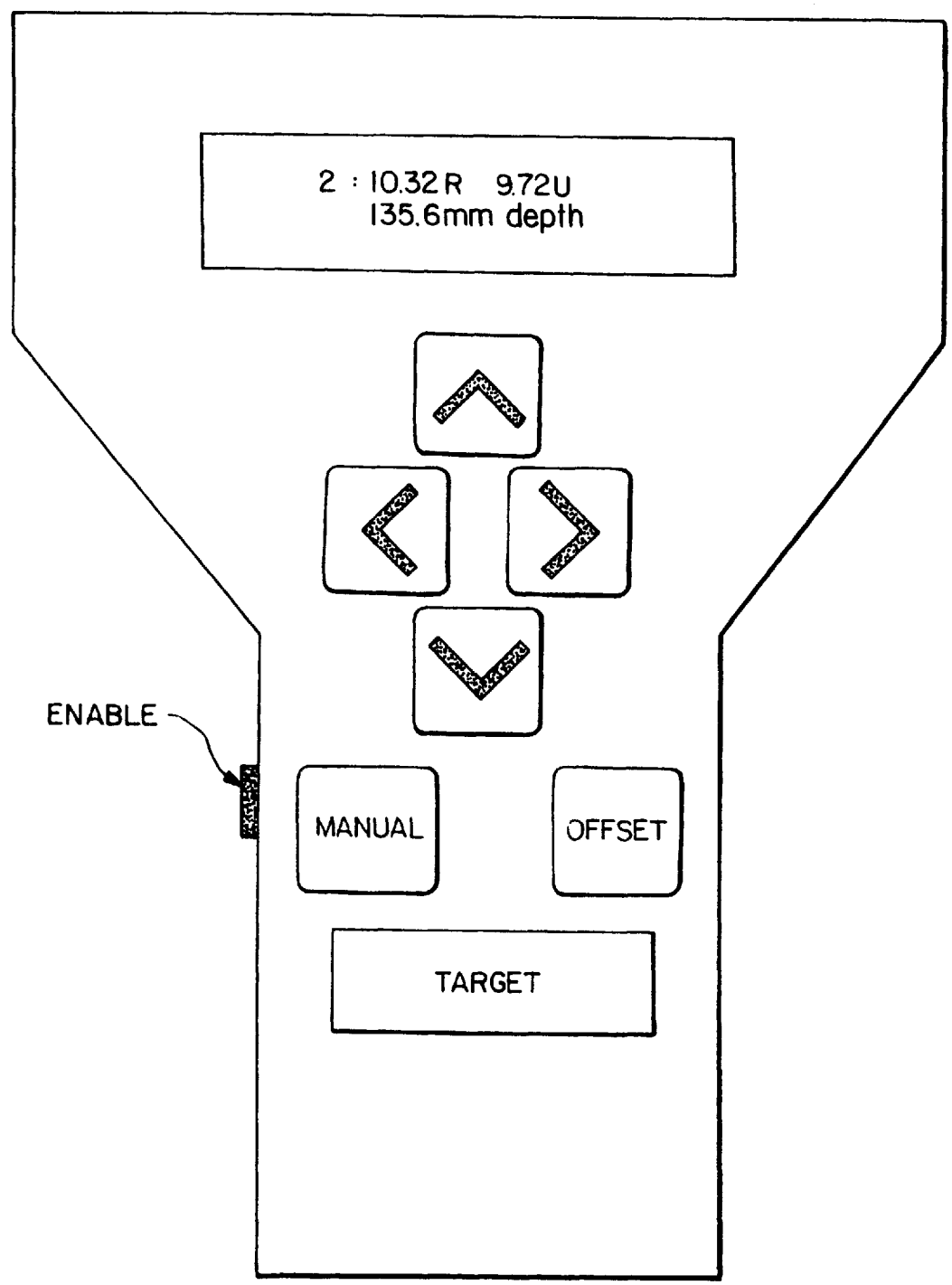
FIG. 4 is a pictorial diagram of the operator hand controller of FIG. 1.
Figure 5:
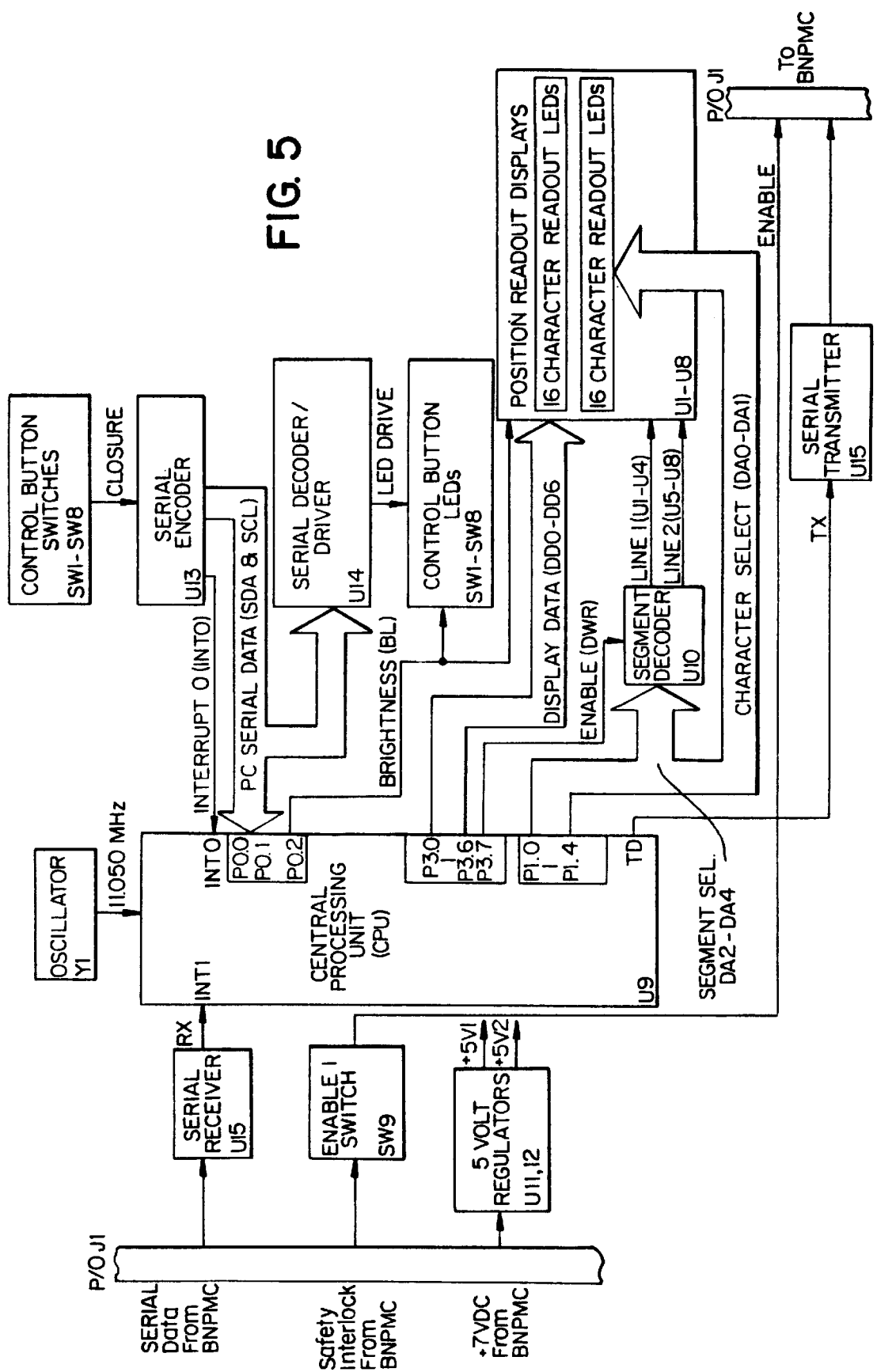
FIG. 5 is a detailed block diagram of circuitry employed in the operator hand controller of FIGS. 1 and 4.

Referring now to FIGS. 4 and 5, it will be understood how the operator hand controller of FIG. 4 transmits data to and receives data and instructions from the biopsy needle positioning motor controller via an RS422 serial transmitter/receiver bus (serial channel A). While the operator hand controller is described herein as being a hand-held unit, it may also comprise a console or table-mounted unit. The principal functions of the operator hand controller are to 1) transmit switch closure data resulting from actuation of the direction arrow keys and the MANUAL, OFFSET, and TARGET keys to the biopsy needle positioning motor controller; 2) illuminate button LEDs in accordance with information received from the biopsy needle positioning motor controller; and 3) display the spatial coordinates of the identified point of interest within the patient's breast, as provided by the biopsy needle positioning motor controller. Additionally, the operator hand controller provides a safety interlock through the ENABLE switch SW9, which must be simultaneously depressed by the user with a selected one of the function keys in order to initiate any of the functions of the operator hand controller. The ENABLE switch is mounted on the side of the operator hand controller and, when depressed, energizes a relay in the biopsy needle positioning motor controller that enables movement of the biopsy needle positioning mechanism. When this switch opens, the relay removes power from the three DC motors 12, 14, and 16 of the biopsy needle positioning mechanism.

The clinician user initiates control of the biopsy needle positioning mechanism in either an automatic or manual mode by depressing control switches on the operator hand controller. Depressing one of the arrow keys or one of the MANUAL, OFFSET or TARGET keys has the effect of grounding a corresponding input of serial encoder U13. This causes serial encoder U13 to apply an INTERRUPT 0 (INT00) to the CPU U9 and place the serial data in 12C protocol on the serial lines SDA and SCL to the CPU U9. The CPU U9 converts the switch information to RS422 protocol and sends it to the biopsy needle positioning motor controller via serial transmitter U15. Each of the keys on the operator hand controller contains a light emitting diode LED that is illuminated under the control of the biopsy needle positioning motor controller. The biopsy needle positioning motor controller selects a particular LED to be illuminated, sets the brightness of that LED, and determines how long that LED is to remain illuminated. This information is sent to the CPU U9 via serial receiver U15. The CPU U9 then places the information in 12C protocol on the serial lines SDA and SCL to be transmitted to serial decoder/driver U14. Serial decoder/driver U14 pulls a corresponding output to its low state, thereby illuminating the selected LED. The CPU U9 controls the brightness of the LEDs on the operator hand controller by setting the duty cycle of BRIGHTNESS (BL) pulses applied to the LEDS. A 50% duty cycle illuminates the LEDs at half brightness and a 100% duty cycle illuminates the LEDs at full brightness.

The position readout displays U1–U8 in the operator hand controller provide two rows of displayed information comprising 16 ASCII characters in each row. Each row comprises four display devices, and each display device contains four 5×7 dot matrix character displays. Referring to FIG. 4, the top line of the position readout display Indicates target number 2 (2:), a rotation axis angle of 10.32 degrees right (10.32R), and an angulation axis angle of 9.72 degrees up (9.72U). The bottom line of the position readout display indicates a depth stop setting of 135.6 millimeters (135.6 mm depth). As previously described in connection with the LEDs that illuminate each of the keys of the operator hand controller, the biopsy needle positioning motor controller similarly controls the position readout displays through serial communications with the operator hand controller CPU U9. The CPU U9 provides segment selection control and character display using two data buses DD0–DD7 and DA0–DA4. To display a selected ASCII character, the CPU U9 puts data describing the character on the DD0–DD7 (P3.0–P3.6 outputs of the CPU is U9) bus. The CPU U9 transmits a low signal ENABLE (DWR) to segment decoder U10, which decodes bits DA2–DA4 and applies a low enable signal to the appropriate ones of display device U1–U8. The enabled display device then decodes the character select bit DA0 and DA1 to select the character position which displays the ASCII character defined by data bus DD0–DD6. As with the LEDs, the biopsy needle positioning motor controller defines the brightness of the position readout display. The biopsy needle positioning motor controller communicates the brightness level to the CPU U9, which then switches the BRIGHTNESS (BL) signal on and off, producing the designated duty cycle.

Figure 6:
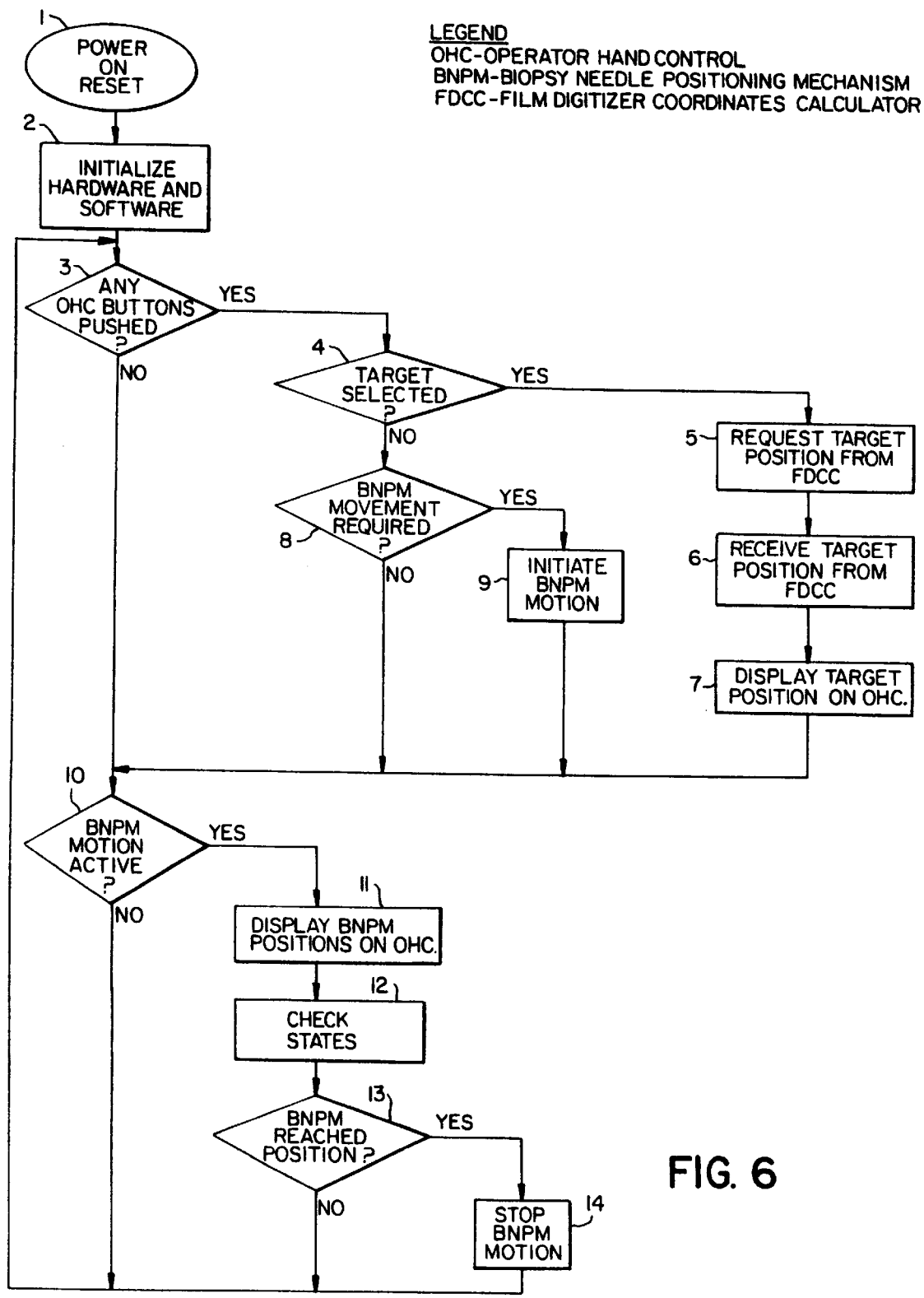
FIG. 6 is a flow chart of the software program executed by the biopsy needle positioning motor controller of FIGS. 1 and 3.
Figure 9C:
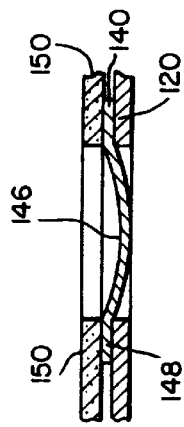
FIG. 9C is a plan view of the portion of the patient table of FIG. 9A that includes the breast aperture and diaphragm cover.
Figure 9B:
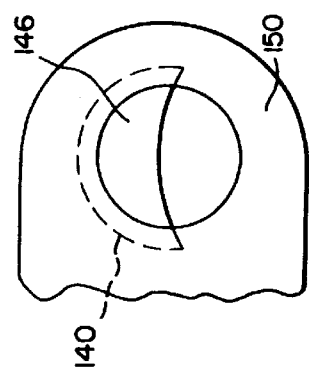
FIG. 9B is a cross sectional view of a portion of the patient table of FIG. 9A illustrating the positioning of the diaphragm cover between the table base and a padded cover therefor.

Referring now to FIG. 6, there is shown a flow chart of the principal software program performed by the biopsy needle positioning motor controller, All of the software represented by the flow chart of FIG. 6 is stored in EPROMs U1 and U6 of the biopsy needle positioning motor controller and is conventionally written in 8051 assembly language. In accordance with block 1 of the flow chart, the software performs several tasks on initialization of the motorized biopsy needle positioner. When power is first applied, to the system, the reset circuit U23 within the biopsy needle positioning motor controller applies a CPU reset pulse to the 8032 CPU (U1). This reset pulse drives the 8032 CPU to its initialization routine.

In accordance with block 2 of the flow chart of FIG. 6, following the power on reset, the 8032 CPU initiates power on reset diagnostics (PRD) which are a series of low level tests of the system hardware to determine whether or not the hardware is working well enough to permit operation to continue. If the power on diagnostics are executed successfully, the 8032 CPU begins performing a number of hardware and software initialization tasks. These include 1) initializing the input/output (I/O) ports on the operator hand controller and biopsy needle positioning motor controller; 2) setting the output ports on the operator hand controller and biopsy needle positioning motor controller to default conditions; 3) clearing the input poets and memory locations of RAM 15 in the biopsy needle positioning motor controller; 4) resetting smart controllers U16 and U17 within the biopsy needle positioning motor controller and loading control parameters; 5) reading the operating program stored in EEPROMs U1 and U6 into the RAM portion of memory U15; 6) setting up the 8032 CPU internal timer 1 for 10-msec periodic interrupt; 7) setting up the 8032 CPU internal timer 0 for 9600 baud rate; 8) setting up the 8032 internal universal synchronous receiver/transmitter (UART) for debug terminal/remote display; 9) initialization of dual UWRT (DUART U20) in the biopsy needle positioning motor controller for serial data transfers; and 10) performing miscellaneous variable initialization as required.

In accordance with block 3 of the flow chart of FIG. 6, following initialization, the 8032 CPU checks the condition of the key state byte sent by the operator hand controller via serial communication channel A and stored in is RAM U15. If the operator hand controller has sent an INT0 byte indicating that a key has been depressed, the software branches to interrogation block 4. If no keys have been depressed, the software increments to interrogation block 10.

In accordance with block 4 of the flow chart of FIG. 6, the 8032 CPU checks the key state byte stored in RAM U15 to determine if the key depressed is the TARGET key. If so, the software branches to routine block 5. It the TARGET key has not been depressed, the software increments to interrogation block 8.

In accordance with block 3 of the flow chart of FIG. 6, the 8032 CPU sends a request for the spatial coordinates or the identified point of interest within the patient's breast to the film digitizer and coordinates calculator via serial communications channel B and through DUART U20. The software then increments to routine block 6.

In accordance with block 6 of the flow chart of FIG. 6, the film digitizer and coordinates calculator responds to a request for spatial coordinates by sending a formatted data package containing those spatial coordinates. This data package is automatically stored in the XDATA buffer section of RAM U15. The software then increments to routine block 7.

In accordance with block 7 of the flow chart of FIG. 6, the 8032 CPU initiates position display on the operator hand controller by storing the data package containing the spatial coordinates of the identified point of interest in the XDATA buffer of RAM U15. The main program initiates transfer of the first character of the display, via serial data communications channel A, and then turns the data transfer task over to an interrupt handler subroutine which completes transfer of the remaining 31 characters of displayed information. When the transfer is complete, the software increments to interrogation block 10.

In accordance with block 8 of the flow chart of FIG. 6, the 8032 CPU checks the key state byte from the operator hand controller to determine if one of the direction arrow keys or the OFFSET key has been depressed, thereby requiring movement of the biopsy needle positioning mechanism. If so, the software branches to routine block 9. If not, the software increments to interrogation block 10.

In accordance with block 9 of the flow chart of FIG. 6, the 8032 CPU loads "go to" data in the motor control circuits for each of the rotation, angulation, and depth axes of the biopsy needle positioning mechanism that represents the current identified point of interest within the patient's breast. In addition to the position data, the 8032 CPU issues start and enable commands to the smart motor controllers U16 and U17. The program then increments to interrogation block 10.

In accordance with block 10 of the flow chart of FIG. 6, the software monitors the feedback position data from the smart motor controllers U16 and U17 to determine if the biopsy needle positioning mechanism is moving. If no movement is detected, the software branches bask to the beginning of the main program loop at interrogation block 3, and the 8032 CPU issues a program loop pulse to the reset circuit. If movement of the biopsy needle positioning mechanism is detected, the program branches to routine block 11.

In accordance with block 11 or the flow chart of FIG. 6, the program monitors the motor position data from the smart motor controllers U16 and U17 on each axis. The new position data is loaded into the XDATA buffer in RAM U15 and the first character is transferred to the operators hand controller via serial communications channel A by the main program. The remaining characters are then transferred by the interrupt handler subroutine. The program then increments to routine block 12.

In accordance with block 12 of the flow chart of FIG. 6, the program checks all status and error information to determine 1) whether any axis has reached a soft limit; 2) whether any axis has reached a hard limit; or 3) whether any current limit been reached. In addition, the smart controller status is chocked to determine 1) whether an excessive position error exists; 2) whether a wraparound error has occurred; or 3) whether an index (center 0) has been detected. The program then increments to interrogation block 13.

In accordance with block 13 of the flow chart of FIG. 6, the 8032 CPU compares current position data to the coordinates of the identified point of interest to determine if the biopsy needle positioning mechanism is properly positioned for insertion of the biopsy needle to the identified point of interest. If it is not at the correct position, the program loops back to interrogation block 3 and the 8032 CPU issues a program loop pulse to the reset circuits. If the biopsy needle positioning mechanism has reached the target position, the program branches to routine block 14.

In accordance with block 14 of the flow chart of FIG. 6, the 8032 CPU issues a status byte to the smart rotor controllers U16 and U17 for each axis, causing the motors to stop. The program then loops back to interrogation block 3, and the 8032 CPU issued a program loop pulse to the react circuits.

As described in detail above, the software flowcharted in FIG. 6 controls the high level modes of operation of the motorized biopsy needle positioner of the present invention. These modes of operation include the JOG mode that enable manual control of the notion of the biopsy needle, the HOME mode that places the biopsy needle in the HOME position, the TARGET mode that drives the biopsy needle into position for insertion to the identified point or interest within the patient's breast, the OFFSET mode that drives the biopsy needle into position for insertion to a point within the patient's breast that is spatially offset from the identified point of interest, and the ERROR mode in which certain error messages are visually displayed to the user. In controlling the modes of operation described above, the software of FIG. 6 processes, key commands received from the operator hand controller, generates messages to be display on the operator hand controller, issues requests to the film digitizer and coordinates calculator for data relating to the spatial coordinates of the identified point of interest, processes data received from the film digitizer and coordinates calculator, issues commands for controlling movement of the biopsy needle positioning mechanism, and performs state machine type processing, In addition, the software flowcharted in FIG. 6 performs motion control by receiving commands from the mode control logic, by generating commands to the smart motor controller U16 and U17 within the biopsy needle positioning motor controller, and by monitoring status during movement of the biopsy needle positioning mechanism. The current motor positions and status information is updated as required for the mode control logic to track the movement of the biopsy needle positioning mechanism. Finally, the software periodically vends messages for display on the remote view and display box. These messages are collected by the interrupt service routine and stored in RAM U15.

In operation, the clinician user initiates a breast biopsy procedure by employing the film digitizer and coordinates calculator to digitize an identified point; of interest within the patient's breast and to then compute the spatial coordinates of that identified point of interest. The computed spatial coordinates appear in the displays of the film digitizer and coordinates calculator, the remote view and display box, and the operator hand controller. The user then employs the operator hand controller to automatically set the biopsy needle positioning mechanism such that the biopsy needle retained therein is precisely positioned for insertion to the identified point of interest by simultaneously depressing the ENABLE and TARGET keys on the operator hand controller. Once the identified point of interest has been sampled, the user may wish to take a biopsy of the surrounding tissue. This is accomplished by entering offsets in as many of the three coordinate axes (rotation, angulation, and depth) as desired. Offsets of 1 to 20 millimeters, in 1-millimeter increments, may be entered by the user. To enter an offset, the user employs the film digitizer and coordinates calculator to place the mouse an one of the stereotactic images of the patient's breast and moves the crosshairs of the mouse above, below, to the right, or to the left of the identified point of interest. The user then clicks the mouse button once for each millimeter of offset desired in that direction. The three displays track the offset entered by the user and display the number of millimeters of offset. The user must simultaneously depress the ENABLE and OFFSFT keys on the operator hand controller to move the biopsy needle positioning mechanism to the offset location. After that biopsy is completed, the user may enter a new offset and repeat the above procedure to obtain a biopsy at another point that is also spatially offset from the original identified point of interest. Alternatively, the biopsy needle positioning mechanism may be returned to the position required for insertion of the biopsy needle to the original identified point of interest by simultaneously depressing the ENABLE and TARGET keys of the operator hand controller.

The user may disregard the identified point of interest and instead select a manual mode of operation to move the biopsy needle positioning mechanism as desired by first simultaneously depressing the ENABLE and MANUAL keys of the operator hand controller. This enables the four directional arrow keys of the operator hand controller, which may then be actuated to provide manual control of the rotation and angulation axes of the biopsy needle positioning mechanism. The user simultaneously depresses the ENABLE key and one of the directional arrow keys to drive the biopsy needle positioning mechanism in the desired direction. The three displays track this movement to provide a visual display of the movement of the biopsy needle positioning mechanism as it occurs. To return the biopsy needle positioning mechanism to the position required for insertion of the biopsy needle to the original identified point of interest within the patient's breast under examination, it is only necessary for the user to simultaneously depress the ENABLE and TARGET keys.

Figure 7:
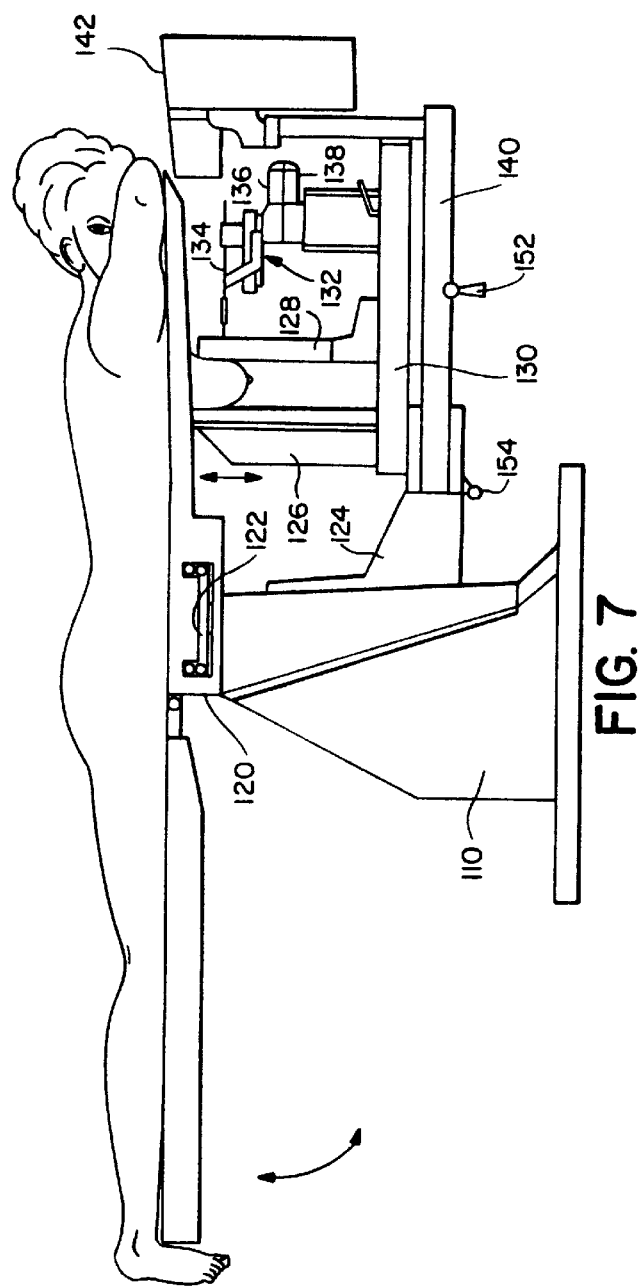
FIG. 7 is a pictorial diagram illustrating a portion of a mammographic needle biopsy system constructed in accordance with the present invention.

Referring now to the pictorial diagram of FIG. 7, there is shown a portion of a mammographic needle biopsy system constructed in accordance with the present invention which incorporates a positioning mechanism such as described above. The system comprises a pedestal base 110, a patient table 120, a film holder arm 130, and an X-ray arm 140. Pedestal base 110 houses conventional electromechanical devices for selectively raising and lowering patient table 120, film holder arm 130, and X-ray arm 140. Alternatively, patient table 120, film holder arm 130, and X-ray arm 140 may be arranged for adjustable inclination from the horizontal to permit medical personnel more working space in which to maneuver film holder ant 130 and X-ray arm 140 beneath patient table 20. The controls for initiating these various mechanical functions are conveniently located on a control handle 122 alongside patient table 120. Film holder arm 130 is supported at one end thereof by an arm carrier 124 and is arranged to pivot radially in a horizontal plane about its connection point to arm carrier 124. X-ray arm 140 is also supported at one end thereof by arm carrier 124 below and in vertical alignment with film holder arm 130 and is also arranged to pivot radially in a horizontal plane about its connection point to arm carrier 124. Primary positions of the film holder arm 130 and X-ray arm 140 are represented by radial movement of plus or minus 90 degrees from the longitudinal axis of patient table 120. Primary detents are provided to lock film holder arm 30 and X-ray arm 140 at their −90, −45, 0, +45, and +90 degree primary positions. Secondary detents are provided to lock the X-ray arm 140 at positions which represent radial motion of plus or minus 15 degrees from each primary position for stereoscopic imaging, as well as at the 0 degree position for general mammography. Independent or simultaneous radial movement of both the film holder arm 130 and the X-ray arm 140 is controlled by locking handles 152 and 154 located-beneath X-ray arm 140. A film holder 126 is mounted-on top of film holder arm 130 proximate the pivot point thereof.

Referring now to the more detailed mechanical diagrams of FIGS. 12A–B and 7, there is shown a support plate 156 attached to arm carrier, 124. A tapered roller bearing assembly 158 resides within support plate 156 and receives a shaft 160 on which X-ray arm 140 is supported for radial motion. A similar tapered roller bearing assembly resides within a support plate 162 and also receives shaft 160 on which film holder arm 130 is supported for radial motion above X-ray arm 140. The use of tapered roller bearings results in substantial elimination of undesirable backlash and play in the support of film holder arm 130 and X-ray arm 140 and thereby increases the overall accuracy of the mammographic needle biopsy system.

A circular detent plate 164 includes a number of wedge-shaped detents 166 spaced around its periphery to lock the film holder arm 130 and X-ray arm 140 into the positions referenced above. An arm assembly lock 168 serves to lock radial motion in concert of film holder arm 130 and X-ray arm 140. Arm assembly lock 168 includes a stationary plate 169 mounted to the underside of arm carrier 124. A locking dog 170 includes an elongated wedge-shaped opening 172 at a pivot end thereof and a lock tab 174 at the other end thereof. Lock tab 174 is wedge-shaped to provide precise mating engagement with wedge-shaped detents 166 around the periphery of circular detent plate 164. A spring 176 urges wedge-shaped lock tab 174 into complete engagement with a selected one of wedge-shaped detents 166. A spring 178 urges the sides of elongated wedge-shaped opening 172 at the pivot end of locking dog 170 into engagement with a circular pivot pin 180 mounted on stationary plate 169. A lever 182, hingedly connected to locking dog 170, is controlled by handle 154 to move wedge-shaped lock tab 174 out of engagement with one of the wedge-shaped detents 166 to permit radial (motion in concert of film holder arm 130 and X-ray arm 140.

An X-ray arm lock 184 is mounted to the underside of X-ray arm 140 and diametrically positioned with respect to arm assembly lock 168, a locking dog 186, similar in shape to locking dog 170, includes an elongated wedge-shaped opening 188 at a pivot end thereof and a lock tab 190 at the other end thereof. Lock tab 190 is wedge-shaped to provide precise mating engagement with wedge-shaped detents 166 spaced around the periphery Of circular detent plate 164. A spring 192 urges wedge-shaped lock tab 190 into complete engagement with a selected one of wedge-shaped detents 166. A spring 194 urges the sides of elongated wedge-shaped opening 188 at the pivot end of locking dog 186 into engagement with a circular pivot pin 196 mounted on the underside of X-ray arm 140. A lever 197 is hingedly connected at pivot point 198 to the underside of X-ray arm 140 and is controlled by either of handles 152 that extend outwardly of the sides of X-ray arm 140 to move wedge-shaped lock tab 190 out of engagement with one of the wedge-shaped detents 166 to permit radial motion of X-ray arm 140 independent of film holder arm 130. The use of wedge-shaped detents 166 on circular detent plate 164, together with precisely mating wedge-shaped lock tabs 174 and 190 that engage therewith results in backlash free locking of film holder arm 130 and X-ray arm 140 to significantly increase the overall accuracy of the mammographic needle biopsy system.

A compression paddle 128 is slidably mounted outwardly from film holder 126 on top of film holder arm 130 and is employed to compress the patient's pendulant breast protruding through an aperture in patient table 120 against film holder 126 preparatory to taking stereoscopic X-ray views thereof. Sliding motion of compression paddle 128 may be controlled manually or by a footswitch coupled to a conventional motorized mechanism. An automatic compression control, which adjustably limits the amount of breast compression, may be provided.

A puncture instrument assembly 132 for retaining a biopsy needle 134 is mounted on top of film holder arm 130 outwardly from compression paddle 128. Puncture instrument assembly 132 is mounted to film holder arm 130 in a conventional manner by means of horizontal and vertical stages whose angular positioning can be automatically controlled as described above in connection with FIGS. 7–12. A depth scale and depth stopper forming part of puncture instrument assembly 132 control the depth to which biopsy needle 134 is inserted into the compressed pendulant breast of the patient during an examination procedure. At least some of the horizontal angle, vertical angle, and insertion depth parameters that define the point of interest within the patient's breast to which biopsy needle 134 is to be inserted are thus automatically set thereby reducing the opportunity for human error. Biopsy needle 134 is conventionally manually inserted into the patient's breast following setting of the proper angle and depth parameter values. However, as the tip of biopsy needle 134 approaches tumorous tissue within the breast, that tissue may tend to move as the needle slowly approaches. In order to avoid this undesirable result, puncture instrument assembly 132 may comprise a conventional spring-loaded biopsy gun for rapidly inserting a biopsy needle to a specific point of interest within the patient's breast. The spring-loaded biopsy gun may comprise, for example, the BIOPTY gun marketed by the Bard Urological Division of C. R. Bard, Inc, Covington, Ga.

A conventional X-ray tube assembly is mounted on top of X-ray arm 140 at the outward end thereof and is arranged to direct an X-ray beam in horizontal alignment with the patient's compressed pendulant breast onto an X-ray film retained within X-ray film holder 126.

Figure 8:
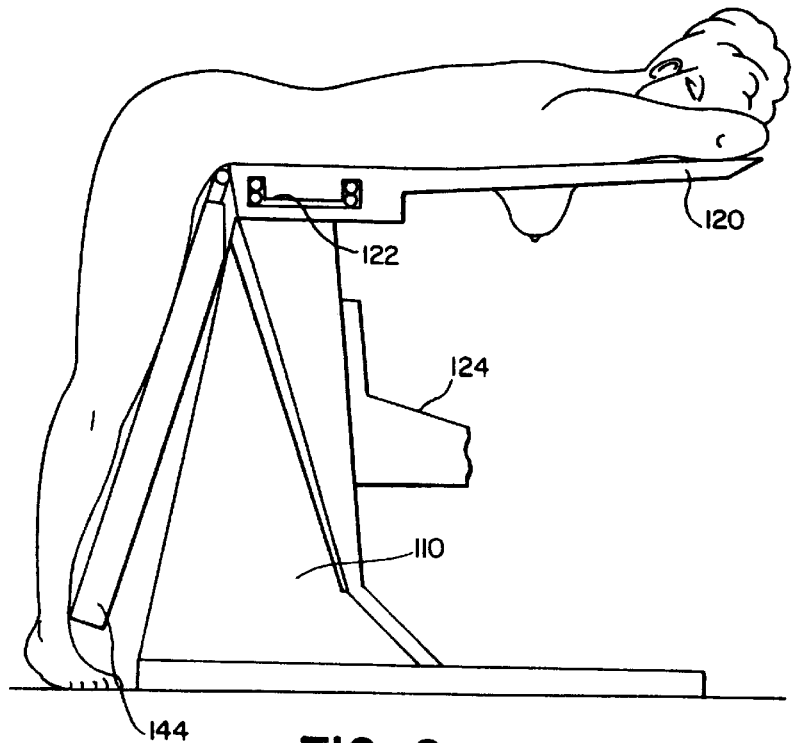
FIG. 8 is a pictorial diagram illustrating the patient table of the mammographic needle biopsy system of FIG. 7 as being hinged to facilitate mounting and dismounting by the patient.

Referring now to the pictorial diagram of FIG. 8, patient table 120 includes a hinged foot portion 144 illustrated in a lowered position to facilitate mounting and dismounting by the patient. Once the patient has positioned herself as shown in FIG. 8, the foot portion of patient table 120 is raised to the horizontal position illustrated in FIG. 7. Similarly, the foot portion 144 of patient table 120 is lowered to the position shown in FIG. 8 following the examination procedure to facilitate dismounting by the patient. Control of the position of foot portion 144 of patient table 120 may be accomplished via any of a number of conventional manual or motorized mechanisms.

Figure 9A:
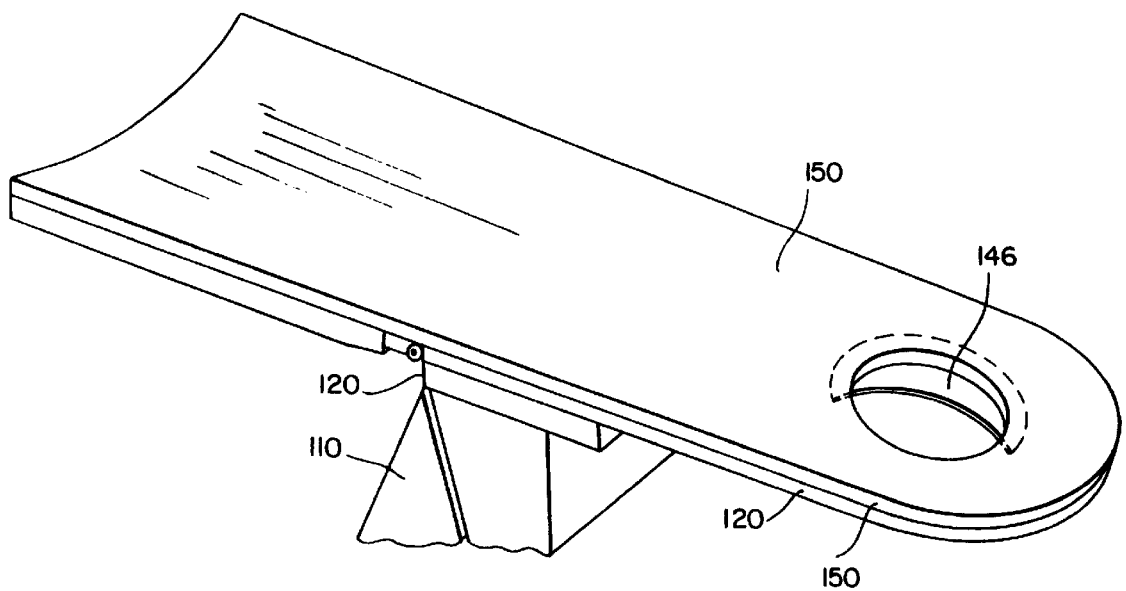
FIG. 9A is a pictorial diagram illustrating the concave surface of the patient table of FIGS. 7 and 8, as well as a breast aperture in the patient table and an associated diaphragm cover therefor.

Referring now to FIG. 9A, there is shown the patient table 120 of FIGS. 7 and 8 formed to be concave in shape along the longitudinal axis thereof to permit examination of the patient's breast tissue that is adjacent the chest wall. A pad 150 covers-table 120 to provide a comfortable surface on which to lie. Also illustrated in FIG. 9A is a breast aperture through which one of the patient's breasts is permitted to pendulantly protrude. Alternatively, table 120 may have a generally flat surface on which the patient lies, but includes a dish-shaped area around the breast aperture to permit examination of the patient's breast tissue that is very near her chest wall. In order to accommodate patients of varying size, a diaphragm cover 146 is provided that may be rotated within the breast aperture to selectively cover a desired portion thereof so that only a selected one of the patient's breasts protrudes through the breast aperture. Diaphragm cover 146 is illustrated in more detail in FIGS. 9B and 9C to include a flange 148 that secures diaphragm cover 146 in place over the breast aperture in patient table 120. Flange 148 is retained between table 120 and pad 150.

Figure 10:
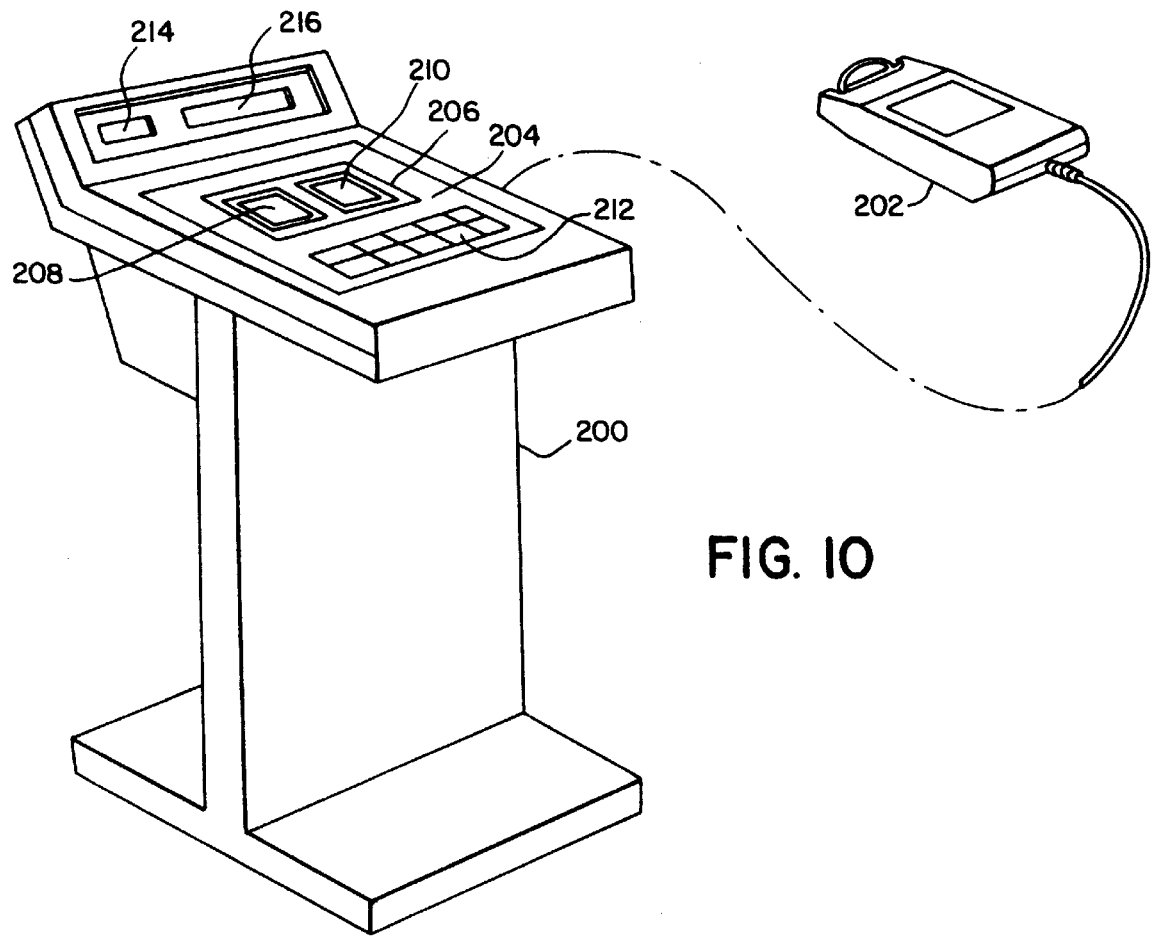
FIG. 10 is a pictorial diagram of a computer-digitizer console and cursor that are employed with the portion of the mammographic needle biopsy system illustrated in FIG. 7.
Figure 15:
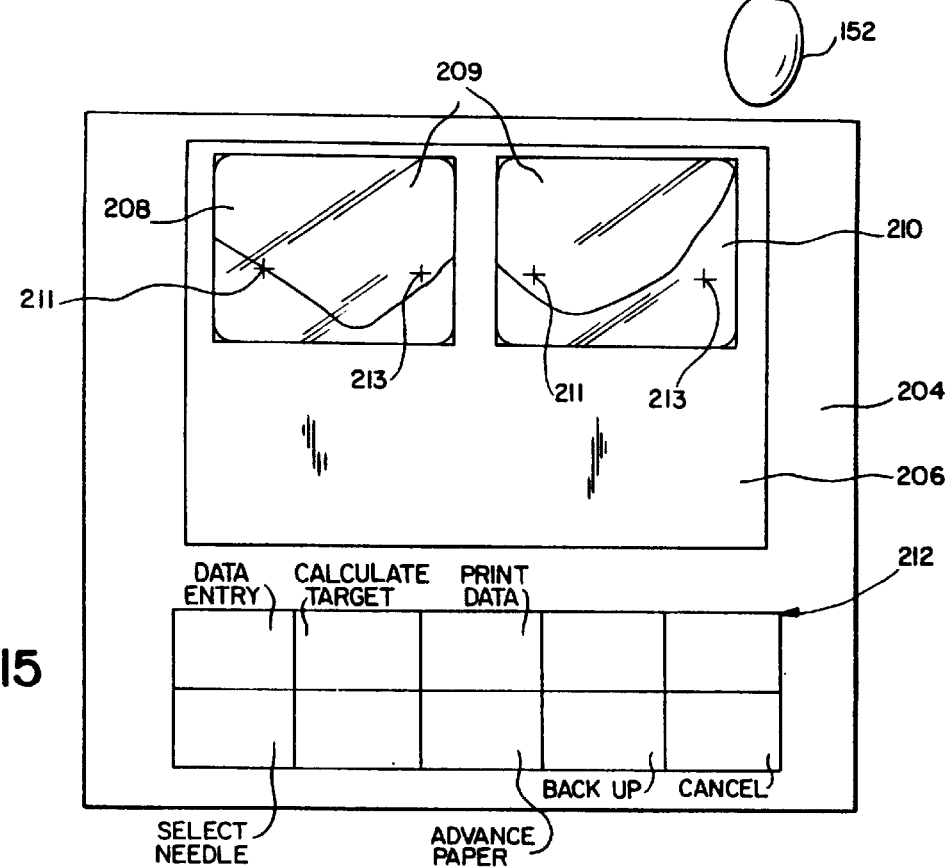
FIG. 15 is a diagram illustrating the layout of the platen area of the computer-digitizer console of FIG. 10.
Figure 14A:
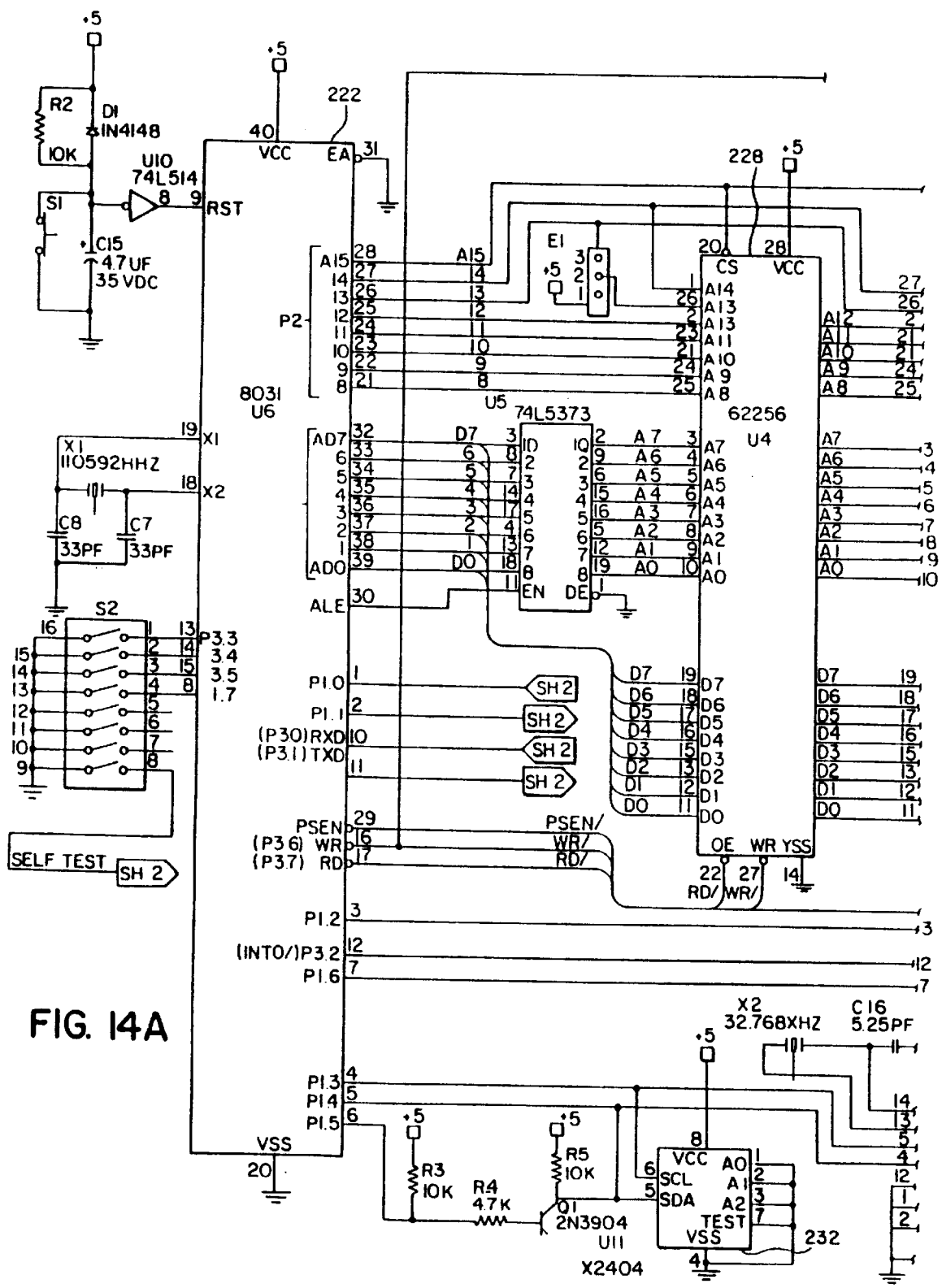
FIGS. 14A–D are a detailed schematic diagram of circuitry employed in the computer-digitizer console and cursor illustrated in the block diagram of FIG. 11.
Figure 14B:
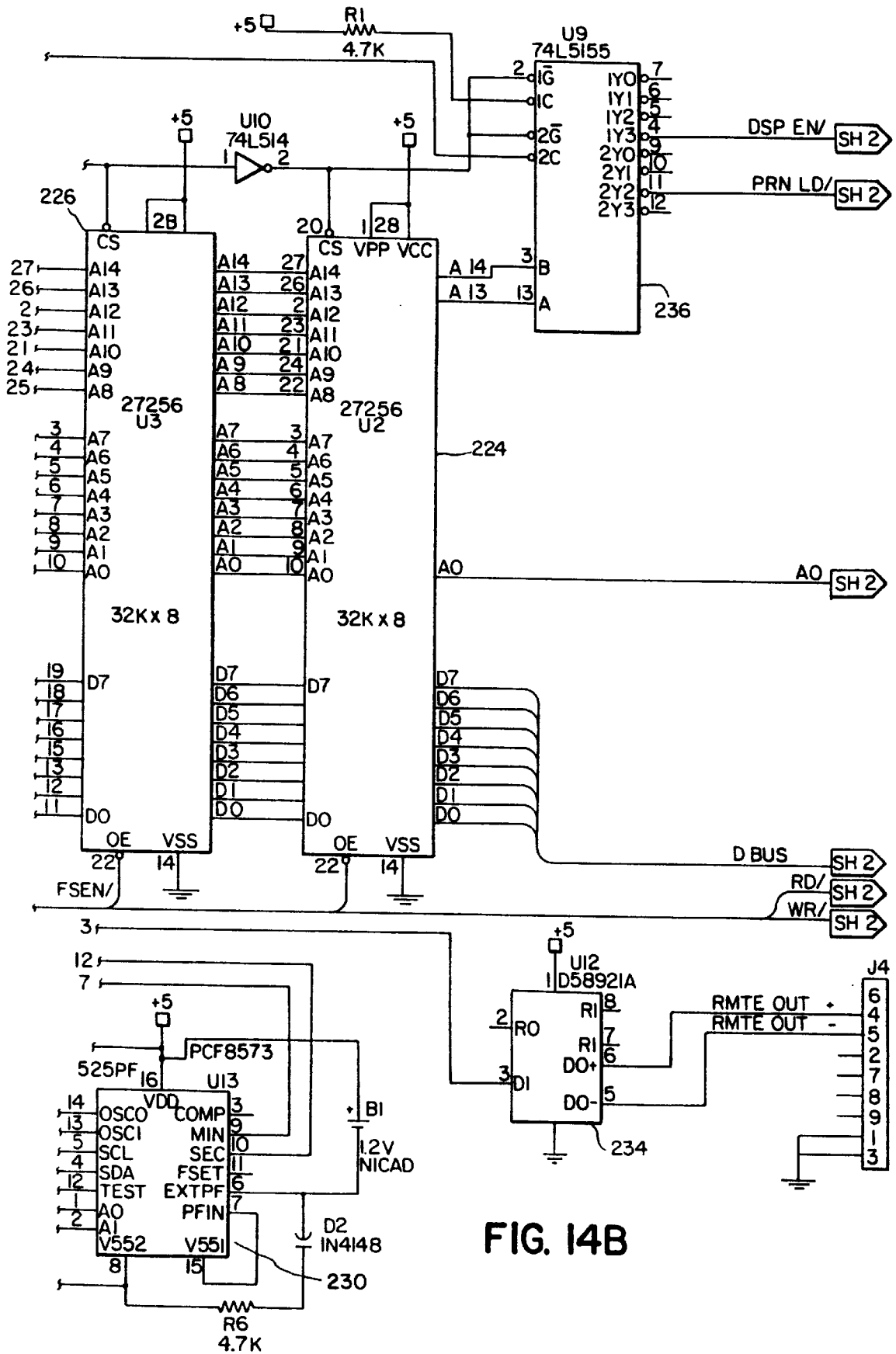
Figure 14C:
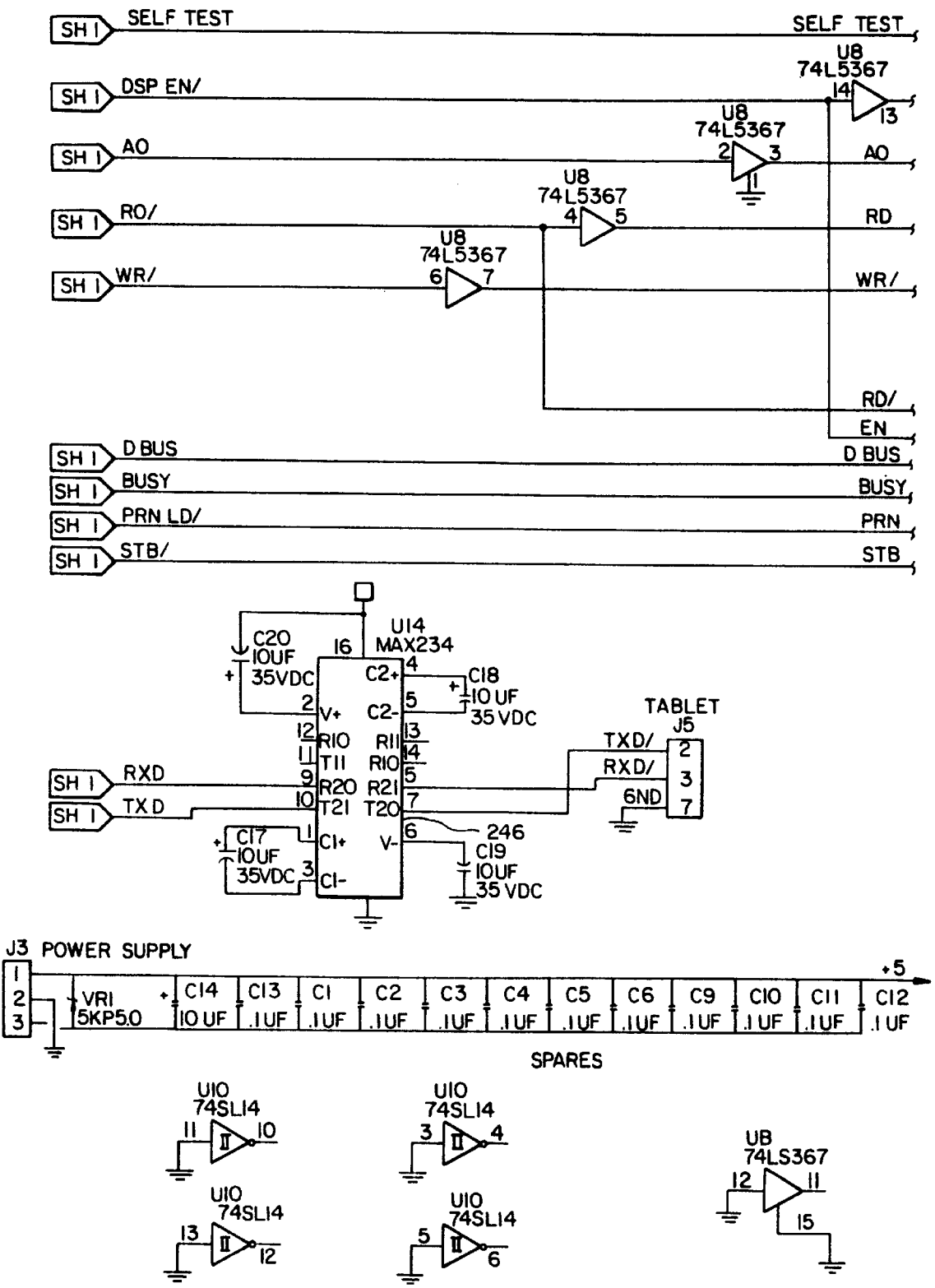
Figure 14D:
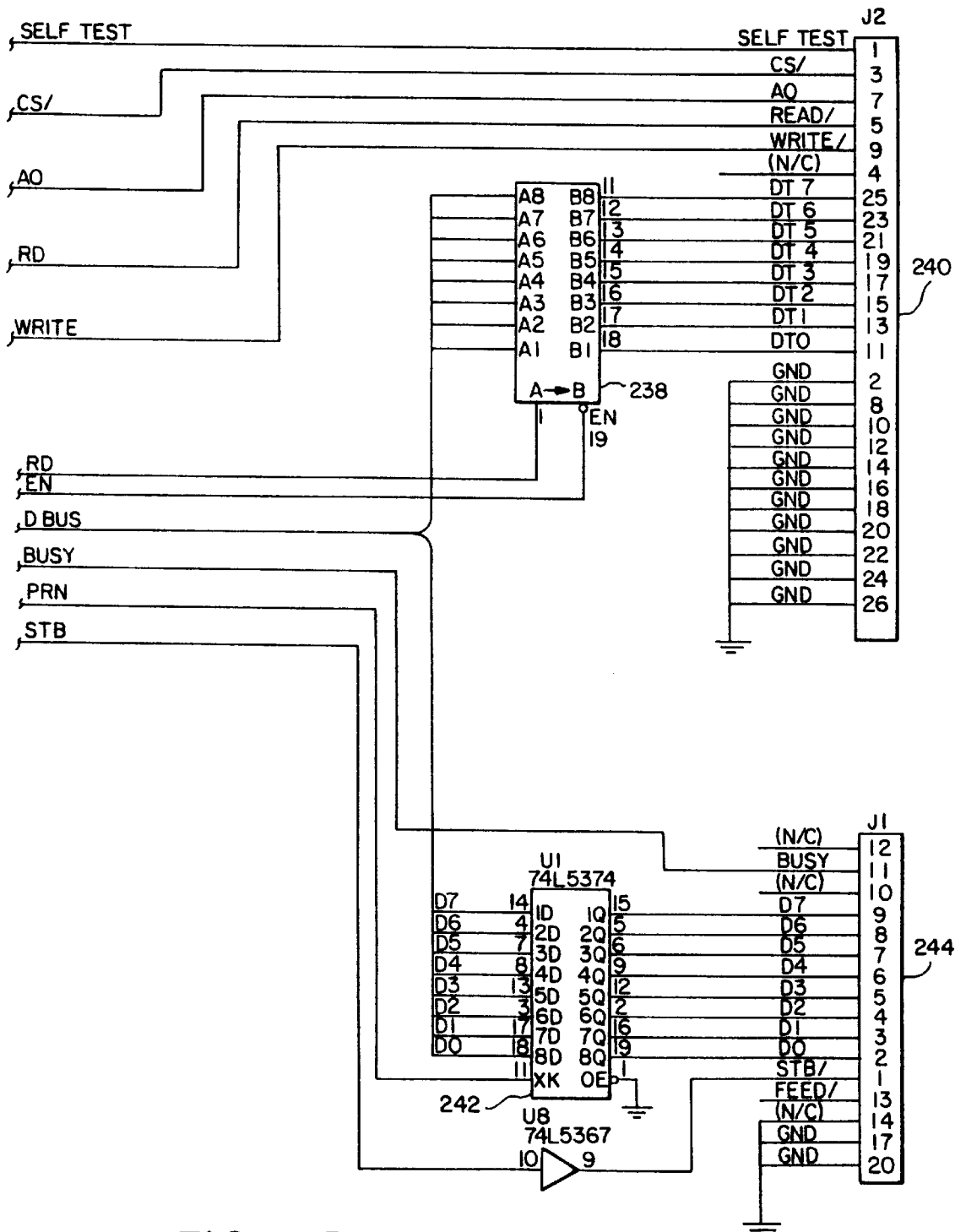

Referring now to FIGS. 10 and 15, there is shown a computer-digitizer console 200 and cursor 202 that are employed to automatically compile information from two stereoscopic X-ray images of the patient's breast. Computer-digitizer console 200 includes a platen area 204 having a light box viewing area 206 over which two stereoscopic X-ray images 208, 210 arc positioned for viewing and digitizing. Platen area 204 also includes a function control area 212 for selecting certain functions to be performed by computer-digitizer console 200. Computer-digitizer console 200 includes a printer 214 for providing a printed record of the vertical angle, horizontal angle, and depth parameters of a point of interest 209 depicted on the two stereoscopic X-ray images 208, 210 and an alphanumeric information display 216 for visually displaying alphanumeric function information selected from function control area 212 of platen area 204, as well as other alphanumeric messages. Cursor 202 is employed on platen area 204 and comprises a one-button mouse with crosshairs that enables the user to select: specific functions specified within function control area 212 of platen area 204 and to digitize a point of interest: 209 depicted on the two stereoscopic X-ray images 208, 210 of the patient's breast.

Computer-digitizer console 200 is operative for analyzing the relative positions of two stereoscopic images 208, 210 taken from two angles and for determining the location in 3-dimensional space of a point of interest 209 shown on the two stereoscopic images 208, 210. In addition, computer-digitizer console 200 is operative for automatically calculating the vertical angle, horizontal angle, and depth of insertion parameters necessary to direct a biopsy needle 134 retained by puncture instrument assembly 132 of FIG. 7 to the point of interest 209 within the patient's breast. The calculations which are made are based on straightforward analytical geometry, and the routines and subroutines of instructions that are executed by computer-digitizer console 200 to perform these calculations are detailed in the firmware listing that follows this specification.

In order to obtain the two stereoscopic images required of the patient's breast, two separate X-rays are taken of the breast from angles of +15 and –15 degrees relative to the normal of the film plane. As a result, a point of interest 209, such as a tumor, shows up in two different positions on each of the two X-ray images 208, 210. Due to the geometry of the present mammographic needle biopsy system, only the X coordinate of the point of interest 209 changes. The Y coordinate remains the same in both X-ray images 208, 210. Thus, when evaluating the two stereoscopic images 208, 210, a point of interest 209 located in the first image 208 is always in the exact vertical plane in the second image 210. The plus and minus 15 degree stereo angle causes the apparent position of an object to translate only in the horizontal plane, never in the vertical plane, A straightedge placed between a pair of projected reference marks I11, 113 on each X-ray image 208, 210 easily defines the horizontal plane to assist in film evaluation. These reference marks are projected with a parallax error in both the X and Y directions because they are not in direct contact with the film but are spaced approximately 10 millimeters away from the film. This parallax error is corrected by way of correction routines executed by computer-digitizer console 200.

Since the geometry of the present mammographic needle biopsy system is known, it is possible to mathematically reconstruct the location of the 3-dimensional breast of the patient with respect to the center of the puncture instrument assembly 132 of FIG. 7 by observing where the breast is projected in the two X-ray stereoscopic images 208, 210. To accurately locate a point of interest 209 depicted on the two stereoscopic X-ray images 208, 210 of the breast, a high resolution digitizer is employed as part of computer-digitizer console 200. Point of interest 209 is located with respect to the absolute reference provided by the two projected reference marks 211, 213 located on each of the two stereoscopic X-ray images 208, 210. The general mathematical technique for aligning an image with a digitizer is to develop a transformation matrix that can accept an input vector defined by the raw X and Y coordinates of the point of interest as determined by the digitizer. These raw coordinates are then transformed mathematically to an output vector defined in terms of X and Y coordinates relative to the system coordinates 0,0 of the two stereoscopic X-ray images 208, 210. The transformation matrix is the result of successively applying translate, rotate, and scale operators to an identity matrix.

The first step in building this transformation matrix is to use knowledge of the location, relative to the file and X-ray source, of the two registration marks 211, 213 projected onto each of the two stereoscopic X-ray images; 208, 210. This sets a reference point for the digitizer. The parallax error in the Y direction is constant since both the left and right registration marks 211, 213 have the same Y coordinates and both positions of the X-ray source are at Y=0. Therefore, the Y coordinate of a line between the two reference marks 211, 213 as they appear on the two stereoscopic X-ray images 208, 210 is constant. Next, using standard principles of analytical geometry, the parallel error in the X direction is calculated for both the left and right reference marks 211, 213 and Is applied to shift the reference marks 211, 213 to their trues locations. Other points appearing on the two stereoscopic X-ray images 208, 210 may now be digitized relative to the two reference marks 211, 213. In summary, a mathematical translation is performed to locate the left reference mark 211 at X=0, Y=0. A mathematical rotation is then performed to bring the right reference mark 113 to location Y=0. Parallax errors are subtracted to determine the true locations of the reference marks 211, 213 so that a point between them can be located. This point arbitrarily becomes location 0,0 of the two stereoscopic X-ray images 208, 210. Subsequently, any digitized point on the two stereoscopic X-ray images 208, 210 is manipulated by the transformation matrix to produce the X and Y coordinates of that point relative to location 0,0 on the images. Thereby, the raw digitizer coordinates are transformed into film coordinates.

After digitizing the point of interest 209 shown on the two stereoscopic X-ray images 208, 210 of the patient's breast, the coordinates of the endpoints of two lines are known. These lines are the two rays that began at the focal point of the X-ray, travelled through the patient's breast, and ended on the surface of the X-ray film. The equation for the intersection of these lines must then be solved. Since the endpoints of these two lines are measured with respect to the same reference, the point of intersection in X, Y, Z space is determined analytically using standard principles of analytical geometry.

Puncture instrument assembly 132 of FIG. 7 provides horizontal angle, vertical angle, and insertion depth control of biopsy needle 134 mounted therein. The location of the rotational isocenter of puncture instrument assembly 132 is known in the X, Y, and Z directions. It is therefore easy to "draw" a line between this rotational isocenter or pivot point and the point of interest 203 shown on the two stereoscopic X-ray images 208, 210. The projection of this line in the X–Z plane is the horizontal coordinate. The other coordinate is vertical and is obtained from the projection of this line in the Y–Z plane, with the exception that the biopsy needle does not radiate from the pivot point. The angle between the horizontal and vertical coordinates Is known as the beta angle. Since the distance that the axis of the biopsy needle 134 is offset from the pivot point is known, a right triangle can be "drawn" using the Y–Z projection and the amount of the needle offset. The third side of this right triangle represents the total distance to the point of interest 209 shown on the two stereoscopic X-ray images 208, 210 of the patient's breast and is used to set the depth to which biopsy needle 134 is to be inserted into the breast to locate the point of interest 209. The angle between the third side of the right triangle and the Y–Z projection is subtracted from the angle beta to determine the elevation or vertical angle. Alternatively, the axis of biopsy needle 134 could be positioned in the same plane as that of the pivot point to avoid the calculations required to take into account any offset distance between the axis of the biopsy needle 134 and the pivot point. The determinations of horizontal and vertical angles are subject to a final correction to account for slight angular errors in aligning the positioners for puncture instrument assembly 132. The determined depth setting takes into account the length of the biopsy needle 134 and of the needle holder of puncture instrument assembly 132.

Figure 11:
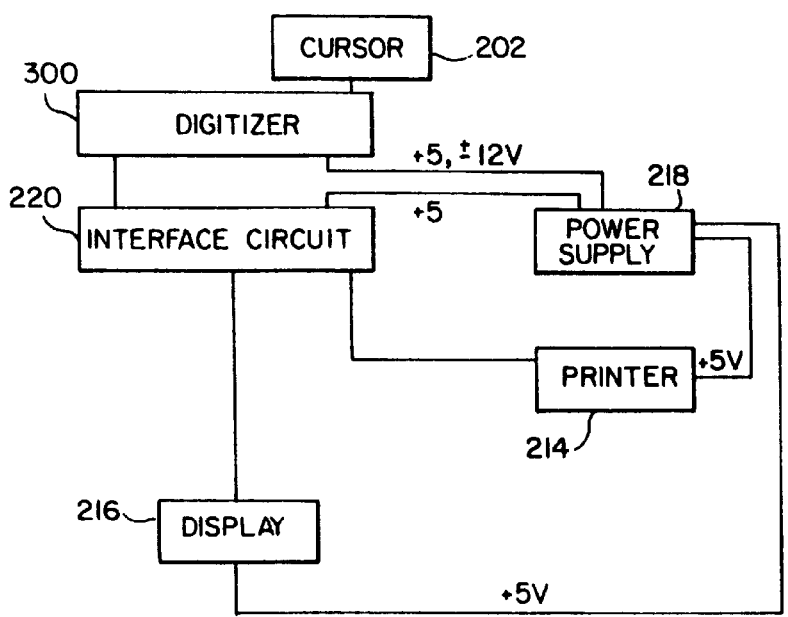
FIG. 11 is an electrical block diagram of the computer-digitizer console and cursor of FIG. 10.
Figure 12:
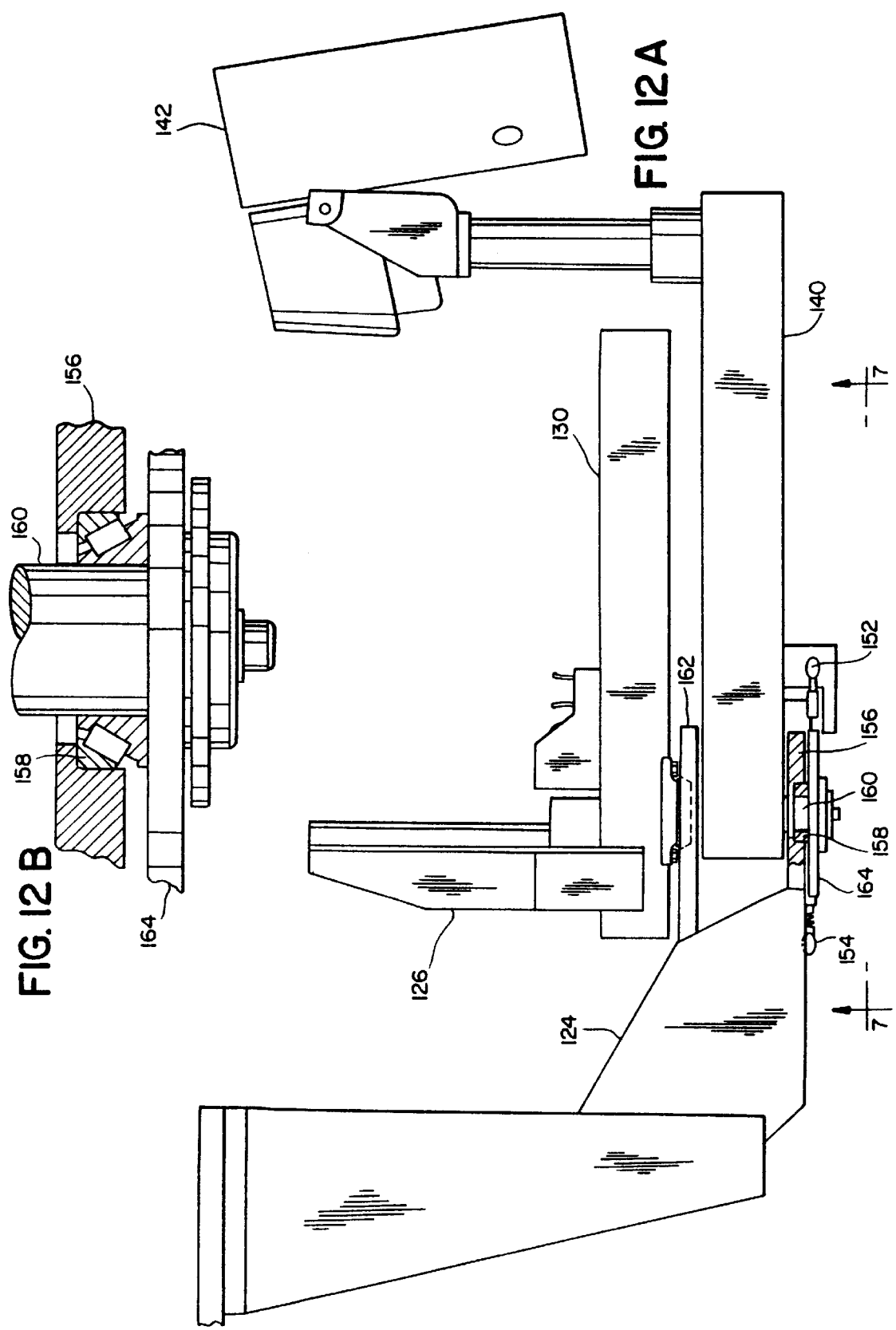
FIG. 12A is a pictorial diagram illustrating the support and locking mechanism for a film holder arm and an X-ray arm that are part of the portion of the mammographic needle biopsy system illustrated in FIG. 7.
FIG. 12B is a cross sectional diagram illustrating the details of a tapered bearing support system for the X-ray arm of FIG. 12A.
Figure 13:
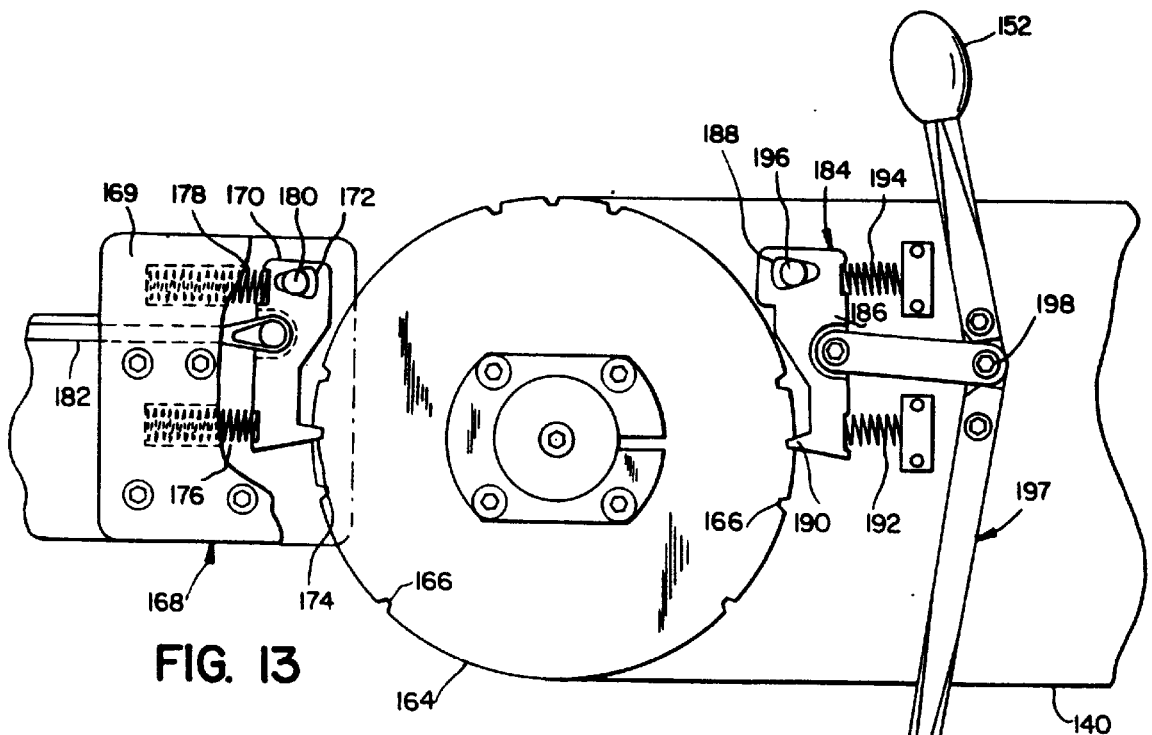
FIG. 13 is a detailed mechanical diagram of the locking mechanism for the film holder and X-ray arms illustrated in FIGS. 7 and 12A.

Referring now to FIG. 11, there is shown a hardware block diagram of computer-digitizer console 200 and cursor 202 of FIGS. 10 and 15. Digitizer 300 may comprise a Model 2200 digitizer manufactured by Numonics, Inc. Digitizer 300 includes a platen 204 that is backlit for viewing two stereoscopic X-ray images 208, 210 of the patient's breast for purposes of digitizing a point or interest 209 depicted on the two stereoscopic X-ray images 208, 210. Cursor 202 may comprise, for example, a one-button mouse with crosshairs, also manufactured by Numonics, Inc. Alphanumeric information display 216 may comprise a flip 2×20 vacuum fluorescent display manufactured by IEE. Printer 214 may comprise a Model STP211-192 printer and associated interface circuitry manufactured by Seiko. A conventional power supply 218 supplies +5, +12 and −12 volts to power digitizer 300, alphanumeric information display 216, printer 214, and a computer and digitizer interface circuit 220. Computer and digitizer interface circuit 220 comprises the circuitry shown in the detailed schematic diagram of FIGS. 14A–D.

Referring now to the detailed schematic circuit diagram of FIGS. 14A–D, computer and digitizer interface circuit 220 includes a central processing unit or CPU 122 that may comprise an off-the-shelf intel 8031 microprocessor. A pair of PROMS 224, 226 that may each comprise a 32K×8 PROM such as the T127256 serve to store the routines and subroutines of instructions detailed in the firmware listing that follows.. this specification. These routines and subroutines of instructions are executed by CPU 222 to calculate the vertical angle, horizontal angle, and insertion depth parameters necessary to direct biopsy needle 134 of FIG. 7 to a precise point of interest within a patient's breast. A random access memory or RAM 228 provides temporary storage of data and other information during execution by CPU 222 of the routines and subroutines of instructions stored in PROMS 224, 226. RAM 228 may comprise, for example, a Hitachi 62565 32K×8 RAM. A system clock 230 may comprise any of a number of commercially available clock chips, such as the Signetics PCF8573 real time clock chip. A non-volatile electrically erasable (EE) ROM 232, that may comprise a Xicor X2404 EE ROM, serves to store calibration data and setup and adjustment parameters relating to the particular mammographic needle biopsy system in which it resides. A line driver 234, that may comprise a National Semiconductor DS8921A RS422 line driver, serves to interface computer and digitizer interface circuit 220 to a conventional remote display (not illustrated) that may be positioned adjacent patient table 120 of FIG. 7 to permit the operator of the mammographic needle biopsy system to view two stereoscopic X-ray images of the patient's breast from his or her operating position. A memory decoder 236, that may comprise a Texas Instruments 74LS155 memory decoder chip, serves to provide operation logic for computer and digitizer interface circuit 220. A buffer 238, that may comprise a Texas Instruments 74LS245 buffer chip, and a, connector 240 serve to interface computer and digitizer interface circuit 220 to alphanumeric information display 216 located in computer-digitizer console 200 of FIG. 10. Similarly, another buffer 242, that may comprise a Texas Instruments 74LS374 buffer chip, and a connector 244 serve to interface computer and digitizer interface circuit 220 to printer 214. Finally, a logic level converter 246, that may comprise a Maxim 14AX232 TTL to RS232 logic level converter, serves to interface computer and digitizer interface circuit 220 to platen area 204 of computer-digitizer console 200 of FIG. 10.

Referring now to FIG. 15, the function control area 212 of platen area 204 includes a control function menu, the individual functions of which are selected using cursor 202. In order to select the DATA ENTRY function, for example, the crosshairs of cursor 202 are positioned over that selected function and the button on cursor 202 is clicked. A series of prompts displayed on alphanumeric information display 216 then requests information regarding the left reference mark 211, the right reference mark 213, and the point of interest 209 depicted on stereoscopic X-ray image 208. In response to these prompts, the operator aligns the crosshairs of cursor 202 over the left and right reference marks 211, 213, clicking the button of cursor 202 over each reference mark. The operator is then prompted to enter the corresponding information from stereoscopic X-ray image 208. When this process has been completed, the message DATA ENTRY COMPLETED is displayed on alphanumeric information display 216.

The SELECT NEEDLE function shown on function control area 212 allows the operator to choose the appropriate biopsy needle for specific depth calculations. Several localizations on a single point of interest 209 may be performed using biopsy needles of different lengths by alternately selecting the SELECT NEEDLE and CALCULATE TARGET functions. Selecting the SELECT NEEDLE function cycles through five choices of biopsy needles.

The CALCULATE TARGET function shown on function control area 212 initiates automatic computation by computer-digitizer console 200 of the vertical angle, horizontal angle, and insertion depth parameters defining point of interest 209. These results are then displayed on alphanumeric information display 216 and remain displayed until the button of cursor 202 is clicked to select another function.

The PRINT DATA function shown on function control area 212 initiates printing of the calculated values of the vertical angle, horizontal angle, and insertion depth parameters on printer 214.

The ADVANCE PAPER function shown on function control area 212 advances the paper on printer 214 for the period of time during which the button on cursor 202 is depressed.

The BACK UP function shown on function control area 212 allows the operator to reenter the previous item of data during a data entry sequence.

The CANCEL function shown on function control area 212 cancels the present operation being performed by computer-digitizer console 200 and returns the system to an idle mode.

Computer-digitizer 200 is also operative for displaying a number of error codes on alphanumeric information display 216. The WRONG ORDER FOR IMAGE POINTS error code is displayed when the operator attempts to enter data via cursor 202 from stereoscopic X-ray image 210 before entering the appropriate data from stereoscopic X-ray image 208, The BAD ORIENTATION OF FILM FOR DIGITIZING error code is displayed when either of the two stereoscopic X-ray images 208, 210 Is mounted on digitizer viewing area 206 in a position such that reference marks 211, 213 are rotated more than 45 degrees from the X axis.

The REF MARKS MORE THAN 2.0 MM OFF error code is displayed when an error has been made in locating the reference marks 211, 213 on either of the two stereoscopic X-ray images 208, 210 using cursor 202.

The OVERFLOW IN MATH ROUTINES error code is displayed in the case of an internal program execution error and should never be observed.

The NOT ALL DATA POINTS TAKEN error code is displayed when the operator omits one of the six points of data depicted on the two stereoscopic X-ray images 208, 210 during the data entry operation. When this error code appears, the operator must re-initiate the data entry sequence using the DATA ENTRY function shown on function-control area 212.

Other system error codes are displayed from time to time to indicate hardware problems within computer-digitizer console 200. For example, the ERROR READING TIME & DATE CLOCK, the ERROR WRITING TIME & DATE CLOCK, and the ERROR VERIFYING TIME & DATE CLOCK error codes are displayed whenever there is a hardware problem with the real time clock 230. The ERROR READING EEPROM and ERROR WRITING EEPROM error codes are displayed whenever there is a problem with the non-volatile set-up memory EEPROM 232. The BAD EEPROM CHECKSUM-DEFAULTS LOADED error code is displayed whenever a problem is detected with a checksum calculation that occurs when data is written to the EEPROM. When this error occurs, default data is automatically used to operate the system, which may result in a calibration error. The PRINTER BUSY TIME-OUT ERROR error code is displayed to indicate that printer 214 did not respond to the last character sent to it. Finally, the DEFAULT CALIBRATION DATA LOADED error code is displayed whenever default calibration data is used rather than calibration data from the non-volatile set-up memory EEPROM 232. When this occurs, the system must be re-calibrated by a qualified technician.

As stated in detail hereinabove, the mammographic needle biopsy system of the present invention functions in accordance with the principle that a tumor which is photographed by X-ray from separate angles relative to the normal of the film plane is projected in different positions on the X-ray film. The coordinates of these projections can then be measured in relation to a pair of crosshairs projected onto the film as the X-ray photographs are being taken. By using standard analytical geometry relationships, the position of a tumor can be calculated very precisely. A puncture instrument assembly is then used to position the tip of a hollow biopsy needle at the center of the tumor, thereby allowing the operator to extract a sample of the tumorous tissue. The tip of the hollow needle can be manually positioned within the breast and then the puncture instrument assembly can be used to drive the needle tip to the location of interest. This procedure can be performed with an accuracy of better than 1.0 mm. Although the system of the present invention recognizes coordinates of the suspected tumor as X, Y, and Z values it translates these coordinates to vertical angle, horizontal angle, and insertion depth parameter values prior to their being visually displayed or printed for the operator.

We claim:

1. A method for performing medical procedures on a patient's breast, comprising the steps of:

a) displaying a first image of said patient's breast corresponding to a first viewpoint;

b) displaying a second image of said patient's breast corresponding to a second viewpoint;

c) providing an input device for obtaining positional information regarding locations of interest within said patient's breast, said input device including a visual cue which is positionable relative to said displayed images, wherein positional data relative to a position of said visual cue is obtained by activating said input device;

d) viewing said displayed images of said patient's breast to identify and determine three-dimensional coordinates of a selected location of interest within said patient's breast by positioning said visual cue relative to said selected location of interest as viewed in said first image of said patient's breast and activating said input device to obtain first image data, positioning said visual cue relative to said selected location of interest as viewed in said second image of said patient's breast and activating said input device to obtain second image data and employing said first image data and said second image data to determine said three-dimensional coordinates of said selected location of interest within said patient's breast; and e) viewing only one of said displayed images of said patient's breast to identify and determine three-dimensional coordinates of at least one offset location which is spatially offset relative to said selected location of interest by positioning said visual cue relative to said offset location as viewed in said only one of said displayed images of said patient's breast and activating said input device to obtain offset data.

2. The method of claim 1, wherein said step e) comprises using said visual cue to determine an offset direction relative to said selected location, wherein said offset direction is defined by said selected location and said offset location, and repeatedly energizing said input device to obtain said offset data.

3. The method of claim 1, further comprising the step of employing a medical instrument to obtain samples from said selected location and said offset location.

4. An apparatus for performing medical procedures on a breast of a patient, comprising:

(a) support means for supporting a patient's breast in an imaging position relative to a predetermined frame of reference;

(b) transmitting means, disposed in predetermined relation to and positionable relative to said predetermined frame of reference, for transmitting an imaging signal through a patient's breast;

(c) receiving means, disposed in predetermined relation to and position able relative to said predetermined frame of reference, in opposing relation to said transmitting means with a patient's breast positioned therebetween, for receiving at least a portion of said transmitted imaging beam passing through a patient's breast and for providing imaging information regarding said received signal portion;

(d) identifying means, employing said imaging information, for identifying locations of interest within a patient's breast so as to permit determination of three dimensional coordinates of said identified locations of interest within said predetermined frame of reference, said identifying means including display means for displaying first and second images of a patient's breast corresponding to first and second imaging viewpoints, respectively, relative to said predetermined frame of reference, and an input means for obtaining positional information regarding said locations of interest within a patient's breast, said input means including a visual cue which is position able relative to said displayed images, wherein positional data relative to a position of said visual cue is obtained by activating said input means, said identifying means including first means for allowing a user to determine three-dimensional coordinates of a selected location of interest within a patient's breast by first viewing said displayed images of a patient's breast, positioning said visual cue relative to said selected location of interest as viewed in said first image of a patient's breast and activating said input means to obtain first image data, secondly, viewing said displayed images of patient's breast positioning said visual cue relative to said selected location of interest as viewed in said second image of a patient's breast and activating said input means to obtain second image data and employing said first image data and said second image data to determine said three-dimensional coordinates of said selected location of interest within a patient's breast; and said identifying means further including second means for allowing a user to determine three-dimensional coordinates of at least one offset location which is spatially offset relative to said selected location of interest by viewing only one of said displayed images of a patient's breast, positioning said visual cue relative to said offset location as viewed in said only one of said displayed images of a patient's breast and activating said input means to obtain offset data.

5. The apparatus of claim 4, further comprising:

motorized means, operatively associated with said identifying means, for positioning a medical instrument relative to said predetermined frame of reference so as to permit said medical instrument to be inserted within a patient's best to said selected location of interest and/or said offset location.

6. The apparatus of claim 4, further comprising means for determining an offset direction relative to said selected Location, said offset direction defined by said selected location and said offset location, wherein said identifying means is operative for obtaining said offset data by repeatedly energizing said input means.

7. The apparatus of claim 4, further comprising means for digitally storing information regarding said identified locations of interest for use in subsequent insertion of said medical instrument within a patient's breast.

* * * * *